United States Patent [19]
Fesik et al.

[11] Patent Number: 5,665,777
[45] Date of Patent: Sep. 9, 1997

[54] BIPHENYL HYDROXAMATE INHIBITORS OF MATRIX METALLOPROTEINASES

[75] Inventors: Stephen W. Fesik, Gurnee; James B. Summers, Jr.; Steven K. Davidsen, both of Libertyville; George S. Sheppard, Wilmette; Douglas H. Steinman, Morton Grove; George M. Carrera, Jr., Des Plaines; Alan Florjancic, Lake Bluff; James H. Holms, Gurnee, all of Ill.

[73] Assignee: Abbott Laboratories, Abbott Park, Ill.

[21] Appl. No.: 555,690

[22] Filed: Nov. 14, 1995

[51] Int. Cl.⁶ .................. A61K 31/19; C07C 255/00; C07C 259/08
[52] U.S. Cl. .................. 514/575; 558/411; 558/412; 558/414; 562/621
[58] Field of Search .................. 558/411, 412, 558/414; 562/621; 514/575

[56] References Cited

U.S. PATENT DOCUMENTS

| | | | |
|---|---|---|---|
| 3,755,603 | 8/1973 | Harrison et al. | 514/571 |
| 4,599,361 | 7/1986 | Dickens et al. | 514/575 |
| 5,036,157 | 7/1991 | Kneen et al. | 562/623 |

FOREIGN PATENT DOCUMENTS

| | | |
|---|---|---|
| 0 489 579 | 6/1992 | European Pat. Off. |
| 0 574 758 | 12/1993 | European Pat. Off. |
| 0 489 577 | 6/1992 | WIPO |
| WO93/20047 | 10/1993 | WIPO |
| WO94/02246 | 2/1994 | WIPO |
| WO94/10990 | 5/1994 | WIPO |
| WO94/02247 | 9/1994 | WIPO |
| WO94/21625 | 9/1994 | WIPO |
| WO95/06031 | 3/1995 | WIPO |
| WO95/09841 | 4/1995 | WIPO |

OTHER PUBLICATIONS

Testa, M.F., and Shapiro, S.L., *J. Med. Chem.*, 1966, 9 (3), 449.

Primary Examiner—Joseph Conrad
Attorney, Agent, or Firm—Monte R. Browder

[57] ABSTRACT

Compounds of formula

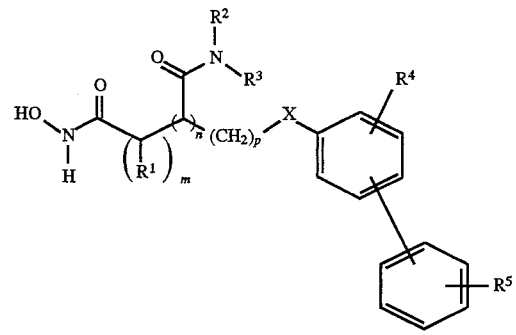

or a pharmaceutically acceptable salt thereof inhibit matrix metalloproteinases and TNFα secretion and are useful in the treatment of inflammatory disease states. Also disclosed are matrix metalloproteinases and TNFα secretion inhibiting compositions and a method for inhibiting matrix metalloproteinases and TNFα secretion.

14 Claims, No Drawings

BIPHENYL HYDROXAMATE INHIBITORS OF MATRIX METALLOPROTEINASES

TECHNICAL FIELD

This invention relates to compounds having activity to inhibit matrix metalloproteinases and TNFα secretion, to pharmaceutical compositions comprising these compounds, and to a medical method of treatment. More particularly, this invention concerns biphenyl hydroxamate compounds which inhibit matrix metalloproteinases and TNFα secretion, to pharmaceutical compositions comprising these, compounds and to a method of inhibiting matrix metalloproteinases and TNFα secretion.

BACKGROUND OF THE INVENTION

The matrix metalloproteinases (MMP's) are a class of extracellular enzymes including collagenase, stromelysin, and gelatinase which are believed to be involved in the tissue destruction which accompanies a large number of disease states varying from arthritis to cancer.

Typical connective tissue cells are embedded within an extracellular matrix of high molecular weight proteins and glycoproteins. In healthy tissue, there is a continual and delicately-balanced series of processes which include cell division, matrix synthesis, and matrix degradation. In certain pathological conditions, an imbalance of these three processes can lead to improper tissue restructuring. For example, in arthritis, joint mobility can be lost when there is improper remodelling of load-bearing joint cartilage. In the case of cancer, lack of coordination of cell division and the two processes of matrix synthesis and degradation can lead to conversion of transformed cells to invasive phenotypes in which increased matrix turnover permits tumor cells to penetrate basement membranes surrounding capillaries leading to subsequent metastasis.

There has been hightened interest in discovering therapeutic agents which bind to and inhibit MMP's. The discovery of new therapeutic agents possessing this activity will lead to new drugs having a novel mechanism of action for combatting disease states involving tissue degenerative processes including, for example, rheumatoid arthritis, osteoarthritis, osteopenias such as osteoporosis, periodontitis, gingivitis, corneal, epidermal or gastric ulceration, and tumor metastasis or invasion.

Tumor Necrosis Factor α (TNFα) is a potent proinflammatory mediator which has been implicated in inflammatory conditions including arthritis, asthma, septic shock, and inflammatory bowel disease. TNFα is originally expressed as a membrane-bound protein of about 26 kD, which is proteolytically cleaved to release a soluble 17 kD fragment (TNFα processing) which combines with two other secreted TNFα molecules to form a circulating 51 kD homotrimer. Recently, several MMP inhibitors were found to inhibit TNFα processing (see Mohler, et al., *Nature*, 1994, 370, 218; Gearing, et al., *Nature*, 1994, 370, 555; and McGeehan, et al., *Nature*, 1994, 370, 558), leading to the hypothesis that TNFα processing is caused by an as yet uncharacterized metalloproteinase residing in the plasma membrane of cells producing TNFα. Inhibitors of this metalloproteinase would therefore be useful as therapeutics to treat disease states involving TNFα secretion.

Certain aryl-substituted hydroxamic acid derivatives which inhibit lipoxygenase and/or cyclooxygenase are described in U.S. Pat. No. 5,036,157. U.S. Pat. No. 3,755, 603 discloses certain biphenyloxyacetohydroxamic acids which are claimed to have antiinflammatory properties.

SUMMARY OF THE INVENTION

In its principal embodiment, the present invention provides a compound of formula

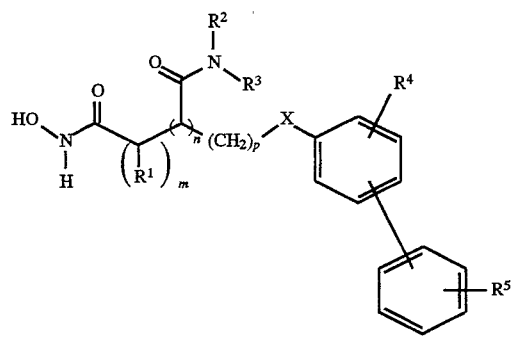

or a pharmaceutically acceptable salt thereof where m and n are independently 0 or 1 and p is 0–6, provided that m, n, and p cannot all be 0.

$R^1$ is selected from the group consisting of (a) hydrogen; (b) alkyl of one to six carbon atoms; (c) alkenyl of two to six carbon atoms; (d) hydroxy; (e)

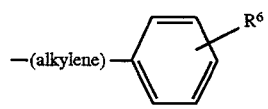

where the alkylene portion is of one to six carbon atoms, and $R^6$ is selected from the group consisting of alkyl of one to six carbon atoms, haloalkyl of one to six carbon atoms, alkoxy of one to six carbon atoms, and hydroxy; (f)

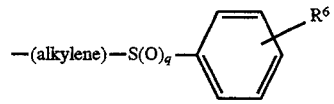

wherein q is 0, 1 or 2, the alkylene portion is of one to six carbon atoms, and $R^6$ is defined above, (g) -(alkylene)-$CO_3R^7$ wherein the alkylene portion is of one to six carbon atoms, and $R^7$ is hydrogen or alkyl of one to six carbon atoms.

$R^2$ and $R^3$ are independently selected from the group consisting of (a) hydrogen; (b) alkyl of one to six carbon atoms; (c) phenyl; (d) phenyl substituted with halogen, alkyl of one to six carbon atoms, haloalkyl of one to six carbon atoms, alkoxy of one to six carbon atoms, or hydroxy; (e) pyridyl, and (f) pyridyl substituted with halogen, alkyl of one to six carbon atoms, haloalkyl of one to six carbon atoms, or alkoxy of one to six carbon atoms.

Alternatively, $R^2$ and $R^3$ taken together with the nitrogen atom to which they are attached define a 5- or 6-membered saturated heterocyclic ring in which the heterocyclic ring optionally contains an additional heteroatom selected from the group consisting of —$NR^8$ wherein $R^8$ is hydrogen or alkyl of one to six carbon atoms, —O—, —S—, or —S(O)$_r$— wherein r is 1 or 2.

X is absent or is selected from the group consisting of (a) —O—; (b) —NH—; and (c) —S—; with the provisos that (a) when X is oxygen, and m and n are zero, p is an integer of two to six, inclusive, and (b) when X is oxygen and m is one and n is zero; then p is an integer of one to six, inclusive.

$R^4$ and $R^5$ are independently selected from the group consisting of (a) hydrogen; (b) alkyl of one to six carbon atoms; (c) halogen; (d) cyano; (e) cyanoalkyl of one to six carbon atoms; (f) haloalllkyl of one to six carbon atoms, (g) hydroxy, and (h) alkoxy of one to six carbon atoms.

The present invention also provides pharmaceutical compositions which comprise a therapeutically effective amount of compound of claim 1 in combination with a pharmaceutically acceptable carrier.

The invention further relates to a method of inhibiting matrix metalloproteinases and/or TNFα secretion in a host mammal in need of such treatment comprising administering to a mammal in need of such treatment a therapeutically effective amount of a compound of claim 1.

DETAILED DESCRIPTION

As used throughout this specification and the appended claims, the following terms have the meanings specified.

The term alkyl refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The terms alkoxy and alkoxyl denote an alkyl group, as defined above, attached to the parent molecular moiety through an oxygen atom. Representative alkoxy groups include methoxy, ethoxy, propoxy, butoxy, and the like.

The term alkenyl as used herein refer to monovalent straight or branched chain groups of 2 to 6 carbon atoms containing a carbon-carbon double bond, derived from an alkene by the removal of one hydrogen atom and include, but are not limited to groups such as ethenyl, 1-propenyl, 2-propenyl, 2-methyl-1-propenyl, 1-butenyl, 2-butenyl and the like.

The term alkylene denotes a saturated divalent hydrocarbon group derived from a straight or branched chain saturated hydrocarbon containing by the removal of two hydrogen atoms, for example —$CH_2$—; —$CH_2CH_2$—, —CH($CH_3$)$CH_2$— and the like.

The term alkenylene denotes a divalent group derived from a straight or branched chain hydrocarbon containing at least one carbon-carbon double bond. Examples of alkenylene include —CH=CH—, —$CH_2$CH=CH—, —C($CH_3$)=CH—, —$CH_2$CH=CH$CH_2$—, and the like.

The terms alkynylene refers to a divalent group derived by the removal of two is hydrogen atoms from a straight or branched chain acyclic hydrocarbon group containing at least one carbon-carbon triple bond. Examples of alkynylene include —C≡C—, —C≡C—$CH_2$—, —C≡C—CH($CH_3$)— and the like.

The term aryl as used herein refers to a monovalent carbocyclic group containing one or more fused or non-fused phenyl rings and includes, for example, phenyl, 1- or 2-naphthyl, 1,2-dihydronaphthyl, 1,2,3,4-tetrahydronaphthyl, and the like.

The term cycloalkyl as used herein refer to a monovalent saturated cyclic hydrocarbon group. Representative cycloalkyl groups include cyclopropyl, cyclobutyl, cyclopentyl, cyclohexyl, cycloheptyl, bicyclo[2.2.1]heptane and the like.

Cycloalkylene denotes a divalent radical derived from a cycloalkane by the removal of two hydrogen atoms.

The term cyanoalkyl denotes an alkyl group, as defined above, substituted by a cyano group and includes, for example, cyanomethyl, cyanoethyl, cyanopropyl and the like.

The term haloalkyl denotes an alkyl group, as defined above, having one, two, or three halogen atoms attached thereto and is exemplified by such groups as chloromethyl, bromoethyl, trifluoromethyl, and the like.

By pharmaceutically acceptable salt is meant those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 1977, 66:1–19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Asymmetric centers may exist in the compounds of the present invention. The present invention contemplates the various stereoisomers and mixtures thereof. Individual stereoisomers of compounds of the present invention are made by synthesis from starting materials containing the chiral centers or by preparation of mixtures of enantiomeric products followed by separation as, for example, by conversion to a mixture of diastereomers followed by separation by recrystallization or chromatographic techniques, or by direct separation of the optical enantiomers on chiral chromatographic columns. Starting compounds of particular stereochemistry are either commercially available or are made by the methods detailed below and resolved by techniques well known in the organic chemical arts.

Compounds contemplated as falling within the scope of this invention include, but are not limited to:
4-(4-phenylphenoxy)butanohydroxamic acid,
4-(3-phenylphenoxy)butanohydroxamic acid,
4-[4-(4-cyanophenyl)phenoxy]butanohydroxamic acid,
4-[4-(3-cyanophenyl)phenoxy]butanohydroxamic acid,
4-[4-(4-cyanomethylphenyl)phenoxy]butanohydroxamic acid,
4-[4-(3-cyanomethylphenyl)phenoxy]butanohydroxamic acid,
4-[4-(4-chlorophenyl)phenoxy]butanohydroxamic acid,
4-[4-(4-propylphenyl)phenoxy]butanohydroxamic acid,
4-[4-(4-methoxyphenyl)phenoxy]butanohydroxamic acid,
7-(4-phenylphenoxy)heptanohydroxamic acid,
7-[4-(4-cyanophenyl)phenoxy]heptanohydroxamic acid,
5-[3-(4-fluorophenyl)phenoxy]pentanohydroxamic acid,
5-[3-(3-cyanophenyl)phenoxy]pentanohydroxamic acid,
5-[3-(4-cyanophenyl)phenoxy]pentanohydroxamic acid, 4-[3-(4-fluorophenyl)phenoxy]butanohydroxamic acid,
4-[3-(4-cyanophenyl)phenoxy]butanohydroxamic acid,
4-[3-(3-cyanophenyl)phenoxyl]butanohydroxamic acid,
5-[3-phenylphenoxy]pentanohydroxamic acid;
5-[4-phenylphenoxy]pentanohydroxamic acid,
5-[4-(4-cyanophenyl)phenoxy]pentanohydroxamic acid,
6-[4-phenylphenoxy]hexanohydroxamic acid,
6-[4-(4-cyanophenyl)phenoxy]pentanohydroxamic acid,
3-(4-phenylphenoxy)propanohydroxamic acid,
3-(3-phenylphenoxy)propanohydroxamic add,
3-[4-(4-cyanophenyl)phenoxy]propanohydroxamic acid,
3-[4-(4-methoxyphenyl)phenoxy]propanohydroxamic acid,
3-[4-(4-fluorophenyl)phenoxy]propanohydroxamic acid,
(S)2-methyl-3-(4-phenylphenoxy)propanohydroxamic acid,
3-(N-methylcarboxamido)-5-[4-(4-cyanophenyl)phenoxy]pentanohydroxamic acid,
3-(4-biphenylthio)propanohydroxamic acid,
3-(4-biphenylthio)ethanohydroxamic acid,
3-(4-biphenylamino)propanohydroxamic acid,
2-(4-biphenyl)ethanohydroxamic acid,
4-(4-biphenyl)butanohydroxamic acid,
4-[4-(4-cyanophenyl)phenyl]butanohydroxamic acid,
3-(4-biphenyl)propanohydroxamic acid,
5-(4-biphenyl)pentanohydroxamic acid,
5-[4-(4-fluorophenyl)phenoxy]pentanohydroxamic acid,
4-(2-hydroxy-4-phenylphenoxy)butanohydroxamic acid,
4-(2-hydroxy-5-phenylphenoxy)butanohydroxamic acid,
3-[4-(3-cyanomethylphenyl)phenoxy]propanohydroxamic acid,
2-tert-butyloxycarbonylmethyl-4-[4-(4-cyanophenyl)phenoxy]butanohydroxamic acid,
3-[4-(4-cyanomethylphenyl)phenoxy]propanohydroxamic acid, and
2-hydroxy-3-[(4-phenyl)phenoxy]propanohydroxamic acid
or a pharmaceutically acceptable salt thereof.

Preferred compounds of the present invention have formula

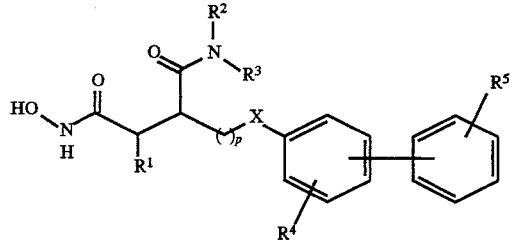

wherein p is 0–6; and $R^1$, $R^2$, $R^3$, $R^4$, $R^5$ and X are defined above.

More preferred compounds of the present invention have formula

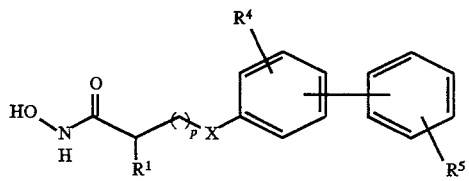

wherein p is 1–6; and $R^1$, $R^4$, $R^5$ and X are defined above.

The most preferred compounds of the present invention have the formula immediately above wherein X is —O—.

DETERMINATION OF STROMELYSIN INHIBITION

The inhibition of stromelysin by the compounds of this invention was determined as follows: Recombinant truncated stromelysin (human sequence) produced in E. coli was prepared by expression and purification of the protein as described by Ye et al., Biochemistry, 1992, 31, 11231–11235. The enzyme was assayed by its cleavage of the thiopeptide ester substrate Ac-Pro-Leu-Gly-[2-mercapto-4-methyl-pentanoyl]-Leu-Gly-OEt described by Weingarten and Feder, Anal Biochem., 1985, 147, 437–440 (1985), as a substrate of vertebrate collagenase. The reported conditions were modified to allow assays to be carried out in a microtiter plate. Upon hydrolysis of the thioester bond, the released thiol group reacts rapidly with 5,5'-dithio-bis(2-nitrobenzoic acid) (DTNB), producing a yellow color which is measured by a microtiter plate reader set al 405 nm. The rates of cleavage of the substrate by stromelysin in the presence or absence of inhibitors are measured in a 30 min assay at ambient temperature. Solutions of the compounds in DMSO are prepared, and these are diluted at various concentrations into the assay buffer (50 mM MES/NaOH pH 6.5 with 10 mM $CaCl_2$ and 0.2% Pluronic F-68), which is also used for dilution of the enzyme and substrate. The potency of the compounds [$IC_{50}$] are calculated from the inhibition/inhibitor concentration data. The compounds of this invention inhibit stromelysin as shown by the data for representative examples in Table 1.

TABLE 1

| Inhibitory Potencies against Stromelysin of Representative Compounds | |
|---|---|
| Example | $IC_{50}$ (µM) or % inhibition |
| 1 | 110 |
| 2 | 5% @ 100 µM |
| 3 | 3.5 |
| 4 | 46 |
| 5 | 21 |
| 6 | 1.9 |
| 7 | 47% @ 100 µM |
| 8 | 10 |
| 9 | 34 |
| 10 | 45% @ 100 µM |
| 11 | 2.3 |
| 12 | 20% @ 100 µM |
| 13 | 24% @ 100 µM |
| 14 | 123 |
| 15 | 74 |
| 16 | 24 |
| 17 | 2.5 |
| 18 | 74 |
| 19 | 38% @ 100 µM |
| 20 | 3.5 |
| 21 | 77 |
| 22 | 1.7 |
| 23 | 0.31 |
| 24 | 14% @ 10 µM |
| 25 | 0.025 |
| 26 | 0.079 |
| 27 | 0.19 |
| 28 | 0.15 |
| 29 | 0.35 |
| 30 | 2.1 |
| 31 | 0.88 |
| 32 | 4.6 |
| 33 | 14% @ 100 µM |
| 34 | 58 |
| 35 | 8.3 |
| 37 | 30 |
| 38 | 1.0 |
| 39 | 47% @ 100 µM |
| 40 | 39% @ 100 µM |
| 41 | 36% @ 100 µM |
| 42 | 0.015 |
| 43 | 0.49 |
| 44 | 0.19 |
| 45 | 2.3 |

TNFα SECRETION INHIBITION

The inhibition of TNFα secretion by the compounds of this invention was determined using a HL-60 TNFα Release Assay. HL-60 cells were cultured in RPMI 1640 with 10% fetal bovine serum and penicillin/streptomycin. HL-60 cells (150,000 cells/well) were placed in 96 well culture plates in RPMI 1640 with 10% fetal bovine serum and pen/strep containing 40 nM phorbol myristate acetate and test compound in DMSO (final DMSO 0.1%). HL-60 cells were then cultured for 20 hr at 37° C. (95% humidity) after which cell supernatants were collected for analysis of TNFα by ELISA. The compounds of this invention inhibit TNFα secretion as shown by the data for representative examples in Table 2.

TABLE 2

Inhibitory Potencies against TNFα secretion of Representative Compounds

| Example | % inhibition @ 16 μM |
|---------|----------------------|
| 1       | 27%                  |
| 4       | 64%                  |
| 5       | 82%                  |
| 6       | 40%                  |
| 7       | 35%                  |
| 8       | 35%                  |
| 11      | 77%                  |
| 12      | 62%                  |
| 13      | 67%                  |
| 14      | 64%                  |
| 15      | 63%                  |
| 18      | 62%                  |
| 19      | 61%                  |
| 20      | 50%                  |
| 24      | 59%                  |
| 34      | 52%                  |
| 38      | 65%                  |

PHARMACEUTICAL COMPOSITIONS

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, marmitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such,as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

PREPARATION OF COMPOUNDS IN THIS INVENTION

The compounds of this invention may be prepared by a variety of synthetic routes. Representative procedures are outlined in the following Schemes 1–4.

The preparation of compounds of formula 5, wherein p is 2–6 and X, $R^4$, $R^5$, and $R^1$ are defined above is described in Scheme 1. Reaction of 1 with haloester 2 (wherein Y is Br, Cl, or I) in the presence of base provides ester 3. Basic hydrolysis of the ester, for example using LiOH or NaOH in an aqueous solvent system such as aqueous dioxane or aqueous methanol, or acidic hydrolysis using, for example, trifluoroacetic acid provides acid 4. Conversion of 4 to the desired hydroxamic acid 5 is accomplished by conversion to the acid chloride using, for example, thionyl chloride or oxalyl chloride, followed by treatment with hydroxylamine or a hydroxylamine equivalent such as O-tert-butyldimethylsilylhydroxylamine.

Scheme 1

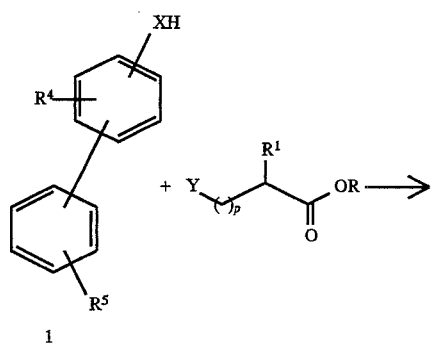

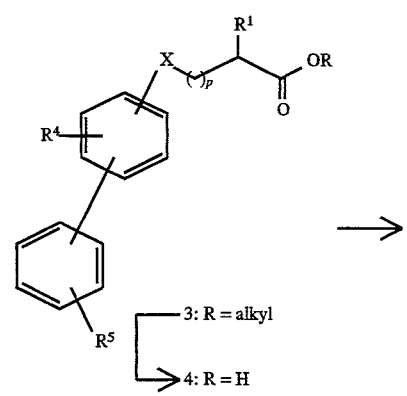

-continued
Scheme 1

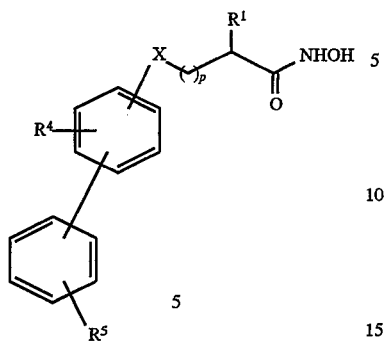

The preparation of the compounds of the invention of formula 7 is outlined in Scheme 2. Reaction of 1, wherein X is O, S, or NH, with β-propiolactone provides acid 6. When X is O or S, a base such as potassium tert-butoxide is required for the lactone opening. Conversion of 6 to the hydroxamic acid 7 is then accomplished as described in Scheme 1 above.

Scheme 2

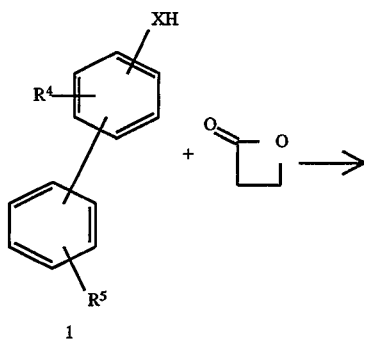

-continued
Scheme 2

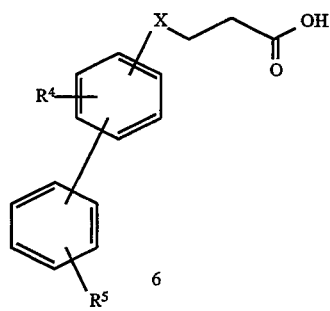

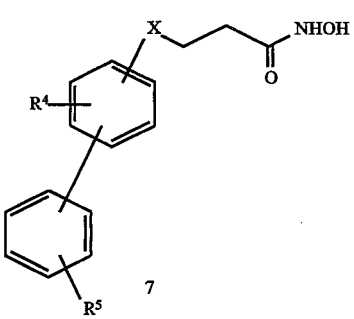

Alternative routes to the compounds of this invention are outlined in Schemes 3 and 4. According to Scheme 3, iodophenyl derivative 8, wherein X is O, S, or NH, is converted to ester 9 as described in Scheme 1 above. The palladium(0)-catalyzed coupling of 9 with phenyl derivative 11, wherein Y is $B(OH)_3$ or trialkyltin, provides the desired biphenyl compound 13. Biphenyl 13 is also obtained by conversion to 9 to the alkyltin compound 10, preferably by reaction with hexamethylditin and palladium(0), followed by coupling with halophenyl compound 12, wherein Y is Br, trifluoromethanesulfonyl, or I, in the presence of palladium (0). A preferred palladium(0) catalyst is tetrakis (triphenylphosphine)palladium(0). Ester 13 is then converted to the hydroxamic acid 5 as described in Scheme 1 above.

Scheme 3

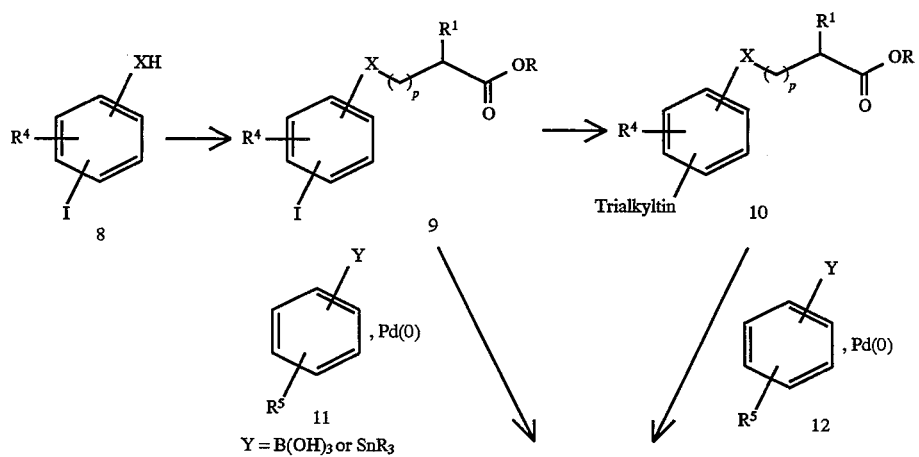

-continued
Scheme 3

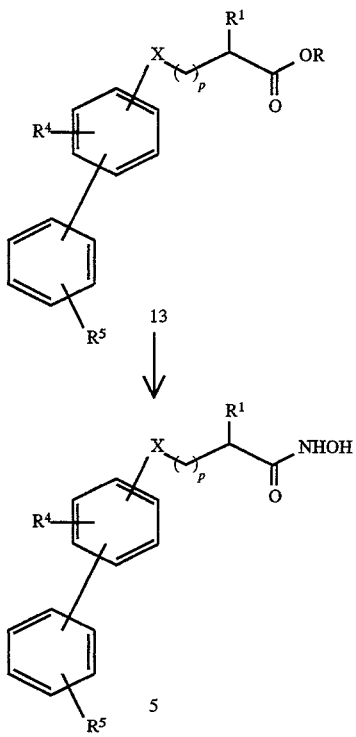

Hydroxamic acid 5, is also prepared from ester 9 as shown in Scheme 4. The ester is hydrolyzed and converted to the O-protected hydroxamic acid 15 as described in Scheme 1 above, except using $H_2NOP$, wherein P is a suitable oxygen protecting group, instead of hydroxylamine. A particularly preferred protecting group is benzyl. Conversion of 15 to the biphenyl derivative 16 is then accomplished by the Pd(0)-catalyzed coupling with phenylboronic acid 11, or by conversion of 15 to the triallcyltin derivative and coupling with halophenyl compound 12 in the presence of Pd(0) as described in Scheme 3 above. Removal of the protecting group, using, for example, catalytic hydrogenolysis when P=benzyl, provides the desired hydroxamic acid 5.

Scheme 4

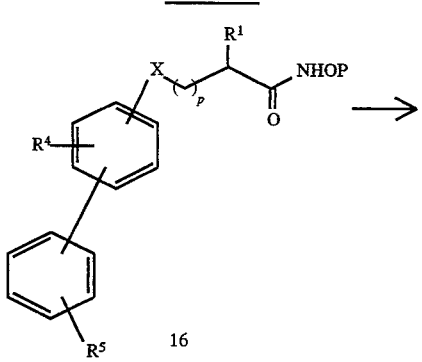

-continued
Scheme 4

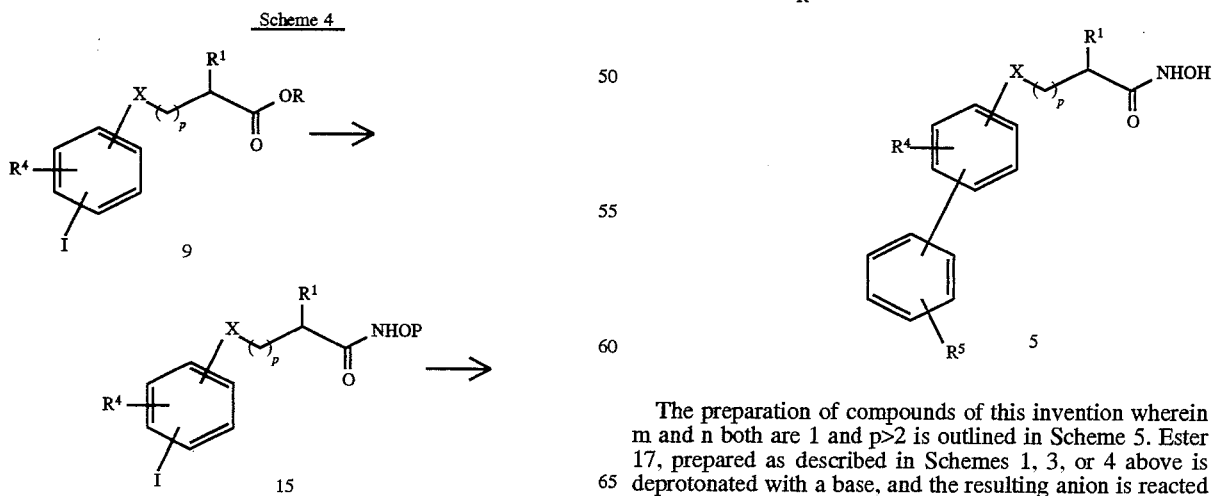

The preparation of compounds of this invention wherein m and n both are 1 and p>2 is outlined in Scheme 5. Ester 17, prepared as described in Schemes 1, 3, or 4 above is deprotonated with a base, and the resulting anion is reacted with a haloester 18 to form diester 19. A representative base useful in this step of the process is lithium hexamethyldisilazide. The groups R and R' are selected such that R can by hydrolyzed in the presence of R'. Preferred groups are ethyl and tert-butyl for R and R' respectively. Selective hydrolysis of 19, for example using aqueous lithium hydroxide when R is ethyl, provides 20, which is then treated with 2 equivalents of a base as defined above followed by addition of alkyl halide $R^1X$. This material is then converted to amide 21 by methods well-known in the art, for example using $HNR^2R^3$ hydrochloride, 1-(3-dimethylaminopropyl)-3-ethylcarbodiimide hydrochloride, and 4-methylmorpholine. Hydroxamic acid 22 is then prepared by hydrolysis of monoester 21, followed by reaction with hydroxylamine as described in Scheme 1.

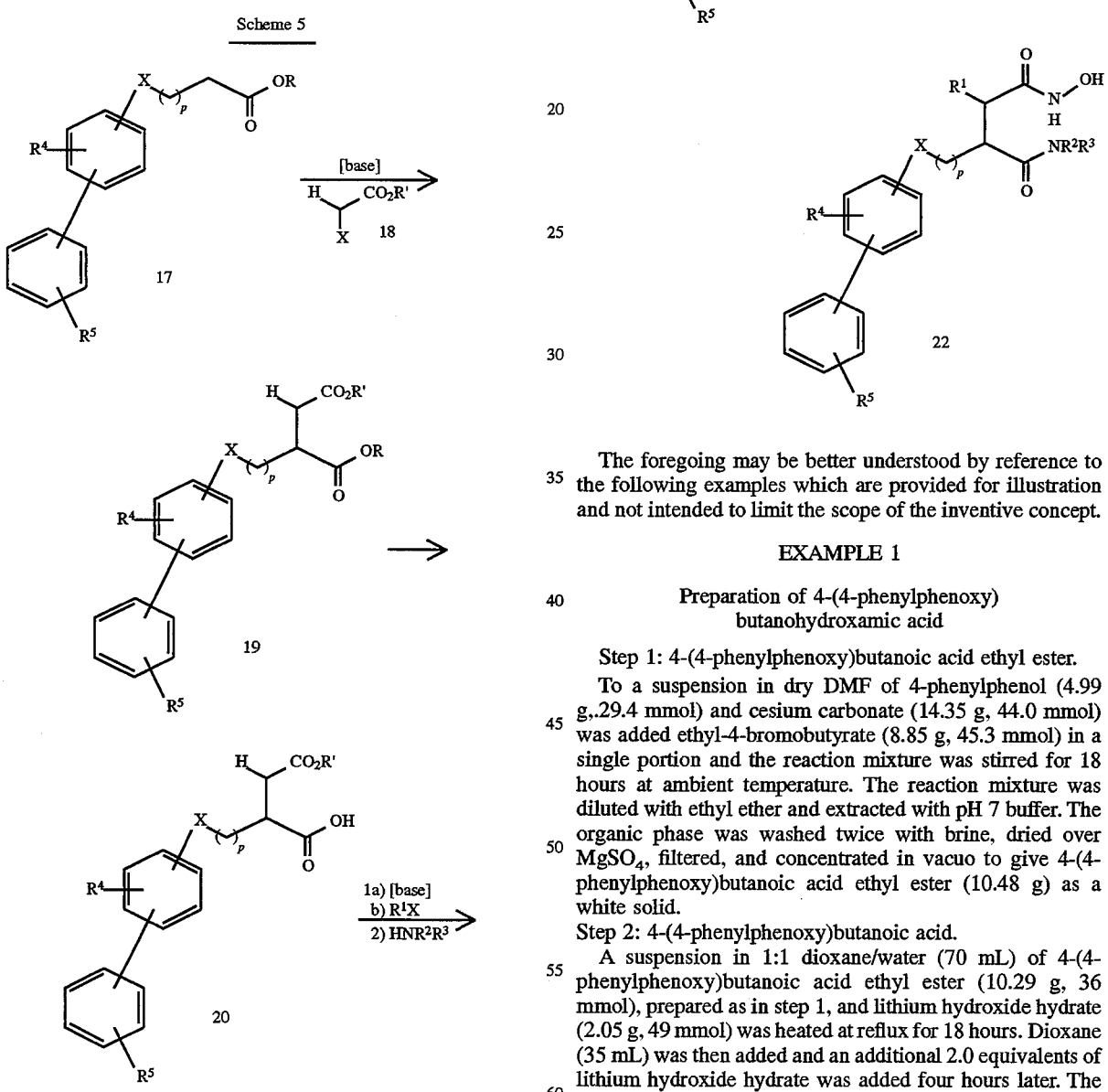

The foregoing may be better understood by reference to the following examples which are provided for illustration and not intended to limit the scope of the inventive concept.

EXAMPLE 1

Preparation of 4-(4-phenylphenoxy) butanohydroxamic acid

Step 1: 4-(4-phenylphenoxy)butanoic acid ethyl ester.

To a suspension in dry DMF of 4-phenylphenol (4.99 g,.29.4 mmol) and cesium carbonate (14.35 g, 44.0 mmol) was added ethyl-4-bromobutyrate (8.85 g, 45.3 mmol) in a single portion and the reaction mixture was stirred for 18 hours at ambient temperature. The reaction mixture was diluted with ethyl ether and extracted with pH 7 buffer. The organic phase was washed twice with brine, dried over $MgSO_4$, filtered, and concentrated in vacuo to give 4-(4-phenylphenoxy)butanoic acid ethyl ester (10.48 g) as a white solid.

Step 2: 4-(4-phenylphenoxy)butanoic acid.

A suspension in 1:1 dioxane/water (70 mL) of 4-(4-phenylphenoxy)butanoic acid ethyl ester (10.29 g, 36 mmol), prepared as in step 1, and lithium hydroxide hydrate (2.05 g, 49 mmol) was heated at reflux for 18 hours. Dioxane (35 mL) was then added and an additional 2.0 equivalents of lithium hydroxide hydrate was added four hours later. The reaction mixture was heated at reflux for two more hours, then was cooled to ambient temperature and concentrated in vacuo. The resulting white solids were shaken with ethyl ether and aqueous 1M NaOH and the residual solid (4-(4-phenylphenoxy)butyric acid, 3.53 g) was filtered off. The organic phase was discarded and the aqueous phase was acidified with concentrated HCl. The aqueous phase was extracted with ethyl acetate. The ethyl acetate extracts were dried over MgSO4, filtered, and concentrated in vacuo to give an additional 6.25 g of 4-(4-phenylphenoxy)butanoic acid.

Step 3: 4-(4-phenylphenoxy)butanohydroxamic acid.

A suspension of 4-(4-phenylphenoxy)butanoic acid (2.42 g, 9.45 mmol) in thionyl chloride (25 mL) was heated at reflux for 90 minutes, during which time the mixture became homogenous. The reaction mixture was cooled to ambient temperature and concentrated in vacuo. The residue was taken up in 1:1 methylene chloride/THF. In a separate flask 4-methylmorpholine (3.5 mL, 32 mmol) was added to a solution of hydroxylamine hydrochloride (2.1 g, 30 mmol) in water (10 mL). THF (20 mL) was then added and the hydroxylamine solution was decanted into the acid chloride solution, and the reaction mixture was vigorously stirred for 2 hours. The reaction mixture was partitioned between saturated aqueous $NH_4Cl$ and methylene chloride. The organic phase was dried over $MgSO_4$, filtered, and concentrated in vacuo to give 4-(4-phenylphenoxy) butanohydroxamic acid (1.45 g) as a white solid. $^1H$ NMR (DMSO-d6) δ 1.94 (m, 2H), 2.14 (t, 2H, J=7 Hz), 4.01 (t, 2H, J=6 Hz), 7.02 (d, 2H, J=8 Hz), 7.29 (t, 1H, J=6 Hz), 7.43 (t, 2H, J=6 Hz), 7.62 (m, 4H), 8.71 (s, 1H), 10.44 (s, 1H). MS (DCI/NH₃) 289 (M+NH₄⁺, 100), 272 (M+H⁺, 35), 255 (30). Anal. Calcd for: $C_{16}H_{17}NO_3$: C, 70.83; H, 6.32; N, 5.16. Found: C, 64.81; H, 6.65; N, 5.82.

EXAMPLE 2

Preparation of 4-(3-phenylphenoxy) butanohydroxamic acid

Step 1: 4-(3-phenylphenoxy)butanoic acid ethyl ester.

The desired compound was prepared according to the method of Example 1, step 1, except substituting 3-phenylphenol for 4-phenylphenol.

Step 1: 4-(3-phenylphenoxy)butanoic acid.

To a solution in 2:1 dioxane/water (36 mL) of 4-(3-phenylphenoxy)butanoic acid ethyl ester (3.42 g, 12 mmol), prepared as in step 1, was added lithium hydroxide hydrate (1.42 g, 33.8 mmol) and the reaction mixture was stirred overnight at ambient temperature. The reaction mixture was concentrated in vacuo and the resulting solid was mostly dissolved in aqueous $Na_2CO_3$. The aqueous solution was decanted from a small amount of residual solid and extracted with ethyl ether. The ether extract was discarded and the aqueous phase was taken to pH 2 with HCl and extracted with ethyl acetate. The ethyl acetate extract was dried over $MgSO_4$, filtered, and concentrated in vacuo to give 4-(3-phenylphenoxy)butanoic acid (3.17 g).

Step 3: 4-(3-phenylphenoxy)butanohydroxamic acid.

The desired compound was prepared according to the method of Example 1, step 3, except substituting 4-(3-phenylphenoxy)butanoic acid, prepared as in step 2, for 4-(4-phenylphenoxy)butanoic acid. $^1H$ NMR (DMSO-d6) δ 1.93 (m, 2H), 2.11 (t, 2H, J=7 Hz), 4.01 (t, 2H, J=6 Hz), 6.92 (d, 1H, J=4 Hz), 6.97 (dd, 1H, J=4, 9 Hz), 7.44 (m, 7H), 10.41 (s, 1H).

EXAMPLE 3

Preparation of 4-[4-(4-cyanophenyl)phenoxy] butanohydroxamic acid

The desired compound was prepared according to the method of Example 2, except substituting 4'-hydroxy-4-biphenylcarbonitrile for 3-phenylphenol. mp 170°–172° C. $^1H$ NMR (DMSO-d6) δ 1.93 (m, 2H), 2.14 (t, 2H, J=7 Hz), 4.02 (t, 2H, J=6 Hz), 7.04 (d, 2H, J=8 Hz), 7.71 (d, 2H, J=8 Hz), 7.86 (m, 4H), 8.64 (s, 1H), 10.40 (s, 1H). IR (KBr) 3310, 2960, 2220, 1680, 1600, 1490, 1245 cm⁻¹. MS (DCI/NH₃) 314 (M+NH₄⁺, 100), 297 (M+H⁺, 40), 253 (70). Anal. Calcd for $C_{17}H_{16}N_2O_3$•0.25 $H_2O$: C, 67.87; H, 5.53; N, 9.31. Found: C, 68.00; H, 5.41; N, 9.08.

EXAMPLE 4

Preparation of 4-[4-(3-cyanophenyl)phenoxy] butanohydroxamic acid

Step 1: 4-(4-iodophenoxy)butanoic acid ethyl ester.

The desired compound was prepared according to the method of Example 1, step 1, except substituting 4-iodophenol for 4-phenylphenol.

Step 2: 4-(4-trimethylstannylphenoxy)butanoic acid ethyl ester.

To a solution in toluene (120 mL) under argon of 4-(4-iodophenoxy)butanoic acid ethyl ester (2.00 g, 5.98 mmol) and hexamethylditin (2.35 g, 7.17 mmol) was added tetrakis (triphenylphosphine)palladium(0) (0.35 g, 0.30 mmol). The reaction mixture was stirred for 15 minutes at ambient temperature and 30 minutes at reflux. The reaction mixture was cooled to ambient temperature, diluted with ethyl acetate, and filtered. The filtrate was washed with pH 7 buffer (NaOH—$KH_2PO_4$) and brine, dried over $Na_2SO_4$, filtered, and concentrated in vacuo. Chromatography on silica gel (40:1, then 20:1, then 10:1 hexane/ethyl acetate) gave 4-(4-trimethylstannylphenoxy)butanoic acid ethyl ester (1.14 g, 51%) as a clear, colorless oil.

Step 3: 4-[4-(3-cyanophenyl)phenoxy]butanoic acid ethyl ester.

To a solution in toluene (27 mL) under argon of 4-(4-trimethylstannylphenoxy)butanoic acid ethyl ester (0.50 g, 1.35 mmol) and 3-iodobenzonitrile (0.46 g, 2.0 mmol) was added tetrakis(triphenylphosphine)palladium(0) (75 mg, 65 μmmol). The reaction mixture was stirred for 10 minutes at ambient temperature and then for 24 hours at reflux.

The reaction mixture was cooled to ambient temperature and diluted with ethyl acetate. The organic solution was decanted away from a fine black precipitate, washed with pH 7 buffer (NaOH—$KH_2PO_4$) and brine, dried over $Na_2SO_4$, filtered, and concentrated in vacuo. Chromatography on silica gel (10:1, then 5:1, then 3:1 hexane/ethyl acetate) gave 4-[4-(3-cyanophenyl)phenoxy]butanoic acid ethyl ester (0.31 g, 74%) as small white opaque rosettes.

Step 4: 4-[4-(3-cyanophenyl)phenoxy]butanohydroxamic acid.

The desired compound was prepared according to the method of Example 2, steps 2 and 3, except substituting 4-[4-(3-cyanophenyl)phenoxy]butanoic acid ethyl ester, prepared as in step 3, for 4-(3-phenylphenoxy)butanoic acid ethyl ester. Pure 4-[4-(3-cyanophenyl)phenoxy] butanohydroxamic acid was isolated by trituration of the crude reaction product with acetonitrile containing 1% trifluoroacetic acid. mp 130°–133° C. $^1H$ NMR (DMSO-d6) δ 1.95 (dt, 2H, J=6.9, 13.8 Hz), 2.15 (t, 2H, J=7.4 Hz), 4.02 (t, 2H, J=6.2 Hz), 7.04 (d, 2H, J=8.8 Hz), 7.63 (t, 1H, J=7.7 Hz), 7.70 (d, 2H, J=8.8 Hz), 7.76 (d, 1H, J=7.7 Hz), 7.98 (d, 1H, J=7.7 Hz), 8.10 (s, 1H), 8.73 (s, 1H), 10.44 (s, 1H). MS (DCI/NH₃) 297 (M+H)⁺, 314 (M+NH₄)⁺. Anal. Calcd for: $C_{17}H_{16}N_2O_3$•0.10$H_2O$ C, 68.49; H, 5.48; N, 9.40. Found: C, 68.37; H, 5.41; N, 9.57

EXAMPLE 5

Preparation of 4-[4-(4-cyanomethylphenyl)phenoxy] butanohydroxamic acid

The desired compound was prepared according to the method of Example 4, steps 3 and 4, except substituting 4-iodophenylacetonitrile for 3-iodobenzonitrile. $^1$H NMR (CD$_3$OD) δ 2.09 (dt, 2H, J=7.4, 14 Hz), 2.30 (t, 2H, J=7.7 Hz), 3.91 (s, 2H), 4.04 (t, 2H, J=6.0 Hz), 7.00 (d, 2H, J=8.8 Hz), 7.40 (d, 2H, J=8.1 Hz), 7.54 (d, 2H, J=8.8 Hz), 7.58 (d, 2H, J=8.1 Hz). MS (DCI/NH$_3$) 311 (M+H)$^+$, 328 (M+NH$_4$)$^+$. Anal. Calcd for: C$_{18}$H$_{18}$N$_2$O$_3$•0.25H$_2$O: C, 68.66; H, 5.92; N, 8.90. Found: C, 68.40; H, 5.58; N, 8.70.

EXAMPLE 6

Preparation of 4-[4-(3-cyanomethylphenyl)phenoxy]butanohydroxamic acid

The desired compound was prepared according to the method of Example 4, steps 3 and 4, except substituting 3-iodophenylacetonitrile for 3-iodobenzonitrile. mp 140°–144° C. $^1$H NMR(CD$_3$OD) δ 2.10 (dt, 2H, J=7, 14 Hz), 2.31 (t, 2H, J=7.4 Hz), 3.95 (s, 2H), 4.04 (t, 2H, J=6.0 Hz), 7.00 (d, 2H, J=8.5 Hz), 7.28 (d, 1H, J=7.4 Hz), 7.42 (t, 1H, J=7.4 Hz), 7.51–7.58 (c, 4H). MS (DCI/NH$_3$) 328 (M+NH$_4$)$^+$. Anal. Calcd for: C$_{18}$H$_{18}$N$_2$O$_3$•0.20 H$_2$O C, 68.86; H, 5.91; N, 8.92. Found: C, 68.92; H, 5.78; N, 8.72

EXAMPLE 7

Preparation of 4-[4-(4-chlorophenyl)phenoxy]butanohydroxamic acid

The desired compound was prepared according to the method of Example 4, steps 3 and 4, except substituting 1-chloro-4-iodobenzene for 3-iodobenzonitrile. mp 168°–170° C. $^1$H NMR (DMSO-d6) δ 1.95 (dt, 2H, J=7, 13 Hz), 2.14 (t, 2H, J=7.7 Hz), 4.00 (t, 2H, J=7 Hz), 7.02 (d, 2H, J=7.7 Hz), 7.47 (d, 2H, J=7.4 Hz), 7.61 (d, 2H, J=9 Hz), 7.64 (d, 2H, J=7.7 Hz), 8.72 (s, 1H), 10.43 (s, 1H). IR Microscope 3279 (m), 3064 (br), 2960 (w), 2804 (br), 1665 (s), 1626 (s), 1607 (s), 1485 (s), 1253 (s), 1200 (m), 811 (s) cm$^{-1}$. MS (DCI/NH$_3$) 306, 308 (M+H)$^+$, 323, 325 (M+NH$_4$)$^+$. Anal. Calcd for: C$_{16}$H$_{16}$NO$_3$Cl•0.40H$_2$O: C, 61.40; H, 5.41; N, 4.48. Found: C, 61.46; H, 5.28; N, 4.33.

EXAMPLE 8

Preparation of 4-[4-(4-propylphenyl)phenoxy]butanohydroxamic acid

The desired compound was prepared according to the method of Example 4, steps 3 and 4, except substituting 4-iodo-1-propylbenzene for 3-iodobenzonitrile. $^1$H NMR (DMSO-d6) δ 0.91 (t, 3H, J=7.4 Hz), 1.61 (dq, 2H, J=7.2, 14.7 Hz), 1.95 (dt, 2H, J=7, 14 Hz), 2.14 (t, 2H, J=7.4 Hz), 2.57 (t, 2H, J=7.6 Hz), 3.99 (t, 2H, J=6.0 Hz), 6.99 (d, 2H, J=8.4 Hz), 7.24 (d, 2H, J=8.1 Hz), 7.52 (d, 2H, J=8.1 Hz), 7.56 (d, 2H, J=8.5 Hz), 8.71 (s, 1H), 10.43 (s, 1H). MS (DCI/NH$_3$) 313 (M+NH$_4$–H$_2$O)$^+$, 314 (M+H)$^+$, 331 (M+NH$_4$)$^+$. Anal. Calcd for C$_{19}$H$_{23}$NO$_3$•0.50H$_2$O•0.25NaCl: C, 67.71; H, 7.18; N, 4.16. Found: C, 68.06; H, 6.94; N, 4.08.

EXAMPLE 9

Preparation of 4-[4-(4-methoxyphenyl)phenoxy]butanohydroxamic acid

Step 1: 4-[4-(4-methoxyphenyl)phenoxy]butanoic acid ethyl ester.

To a solution in ethylene glycol dimethyl ether (30 mL) of 4-(4-iodophenoxy)butyric acid ethyl ester (0.50 g, 1.5 mmol), prepared as in Example 5, step 1, was added tetrakis(triphenylphosphine)palladium(0) (87 mg, 75 μM), and the mixture was stirred for 15 minutes. A solution in ethanol (9.6 mL) of 4-methoxyphenylboronic acid (0.25 g, 1.64 mmol) was then added. Saturated aqueous NaHCO$_3$ (15 mL) was then poured in quickly and the reaction mixture was warmed to reflux and heated for one hour. The reaction mixture was cooled to ambient temperature and concentrated in vacuo. The residue was partitioned between ethyl acetate and 10% aqueous Na$_2$CO$_3$. The organic phase was washed with 10% aqueous Na$_2$CO$_3$ and brine, dried over Na$_2$SO$_4$, filtered, and concentrated in vacuo. Chromatography on silica gel (20:1, then 10:1, then 5:1 hexane/ethyl acetate) gave 4-[4-(4-methoxyphenyl)phenoxy]butanoic acid ethyl ester (0.27 g, 57%) as white feathery needles.

Step 2: 4-[4-(4-methoxyphenyl)phenoxy]butanohydroxamic acid.

The desired compound was prepared according to the method of Example 2, steps 2 and 3, except substituting 4-[4-(4-methoxyphenyl)phenoxy]butanoic acid ethyl ester, prepared as in step 1, for 4-(3-phenylphenoxy)butanoic acid ethyl ester. $^1$H NMR (CD$_3$OD) δ 2.08 (dt, 2H, J=6.8, 13.6 Hz), 2.30 (t, 2H, J=7.4 Hz), 3.80 (s, 3H), 4.01 (t, 2H, J=6.0 Hz), 6.94 (d, 4H, J=8.8 Hz), 7.46 (d, 2H, J=8.5 Hz), 7.46 (d, 2H, J=8.8 Hz). MS (DCI/NH$_3$) 302 (M+H)$^+$, 319 (M+NH$_4$)$^+$. Anal. Calcd for C$_{17}$H$_{19}$NO$_4$•0.40H$_2$O•0.60NH$_4$Cl: C, 59.94; H, 6.57; N, 6.58. Found: C, 60.28; H, 6.50; N, 6.60.

EXAMPLE 10

Preparation of 7-(4-phenylphenoxy)heptanohydroxamic acid

The desired compound was prepared according to the method of Example 2, except substituting 4-phenylphenol for 3-phenylphenol, and substituting ethyl 7-bromoheptanoate for ethyl 4-bromobutyrate. mp 147°–149° C. $^1$H NMR (DMSO-d6) δ 1.32 (m, 2H), 1.41 (m, 2H), 1.52 (p, 2H, J=7 Hz), 1.71 (p, 2H, J=7 Hz), 1.96 (t, 2H, J=7 Hz), 3.99 (t, 2H, J=6 Hz), 7.01 (d, 2H, J=9 Hz), 7.30 (m, 1H), 7.42 (m, 2H), 7.59 (m, 4H), 8.66 (s, 1H), 10.34 (s, 1H). IR (KBr) 3250, 2920, 2845, 1620, 1600, 1520, 1485, 1250 cm$^{-1}$. MS (DCI/NH$_3$) 331 (M+NH$_4$$^+$, 100), 314 (M+H$^+$, 20). Anal. Calcd for C$_{19}$H$_{23}$NO$_3$: C, 72.82; H, 7.40; N, 4.47. Found: C, 72.52; H, 7.34; N, 4.64.

EXAMPLE 11

Preparation of 7-[4-(4-cyanophenyl)phenoxy]heptanohydroxamic acid

The desired compound was prepared according to the method of Example 2, except substituting 4'-hydroxy-4-biphenylcarbonitrile for 3-phenylphenol, and substituting ethyl 7-bromoheptanoate for ethyl 4-bromobutyrate. mp 79°–82° C. $^1$H NMR (DMSO-d6) δ 1.31 (m, 2H), 1.42 (m, 2H), 1.54 (m, 2H), 1.73 (p, 2H, J=7 Hz), 1.96 (t, 2H, J=7 Hz), 4.02 (t, 2H, J=6 Hz), 7.06 (d, 2H, J=9 Hz), 7.70 (d, 2H, J=9 Hz), 7.87 (dd, 4H, J=9, 14 Hz), 8.67 (bds, 1H), 10.36 (s, 1H). IR (KBr) 3280 (br), 2925, 2850, 2230, 1600, 1490, 1250 cm$^{-1}$. MS (APCI (+)) 356 (M+NH$_4$$^+$, 15), 339 (M+H$^+$, 60), 295 (100). Anal. Calcd for C$_{20}$H$_{22}$N$_2$O$_3$: C, 70.99; H, 6.55; N, 8.28. Found: C, 71.08; H, 6.72; N, 6.95.

EXAMPLE 12

Preparation of 5-[3-(4-fluorophenyl)phenoxy]pentanohydroxamic acid

The desired compound was prepared according to the method of Example 4, except substituting methyl 5-bromovalerate for ethyl 4-bromobutyrate, substituting 3-iodophenol for 4-iodophenol, and substituting 1-fluoro-4-iodobenzene for 3-iodobenzonitrile. $^1$H NMR (DMSO-d6) δ 1.71 (m, 4H), 2.04 (t, 2H, J=7 Hz), 4.03 (t, 2H, J=7 Hz), 6.93 (dd, 1H, J=2, 10 Hz), 7.15 (m, 1H), 7.19 (d, 1H, J=8 Hz), 7.27 (t, 2H, J=8 Hz), 7.36 (t, 1H, J=8 Hz), 7.71 (dd, 2H, J=6, 9 Hz), 8.70 (s, 1H), 10.39 (s, 1H). MS (DCI/NH$_3$) 321 (M+NH$_4^+$, 100). Anal. Calcd for: $C_{17}H_{18}FNO_3 \cdot 0.33H_2O$: C, 66.02; H, 6.08; N, 4.53. Found: C, 65.73; H, 5.76; N, 4.38.

EXAMPLE 13

Preparation of 5-[3-(3-cyanophenyl)phenoxy]pentanohydroxamic acid

The desired compound was prepared according to the method of Example 4, except substituting methyl 5-bromopentanoate for ethyl 4-bromobutyrate, substituting 3-iodophenol for 4-iodophenol, and substituting 3-bromobenzonitrile for 3-iodobenzonitrile. $^1$H NMR (DMSO-d6) δ 1.75 (m, 4H), 2.56 (m, 2H), 4.07 (m, 2H), 6.98 (dd, 1H, J=2, 8 Hz), 7.29 (m, 2H), 7.39 (t, 1H, J=7 Hz), 7.66 (dt, 1H, J=1, 7 Hz), 7.83 (dd, 1H, J=1, 8 Hz), 8.03 (d, 1H, J=8 Hz), 8.19 (s, 1H), 8.70 (s, 1H), 10.38 (s, 1H). MS (APCI) 328 (M+NH$_4^+$, 100),311 (M+H$^+$, 90). Anal. Calcd for: $C_{18}H_{18}N_2O \cdot 1.25H_2O$: C, 64.95; H, 6.21; N, 8.42. Found: C, 5.09; H, 5.61; N, 8.14.

EXAMPLE 14

Preparation of 5-[3-(4-cyanophenyl)phenoxy]pentanohydroxamic acid

The desired compound was prepared according to the method of Example 4, except substituting methyl 5-bromopentanoate for ethyl 4-bromobutyrate, substituting 3-iodophenol for 4-iodophenol, and substituting 4-bromobenzonitrile for 3-iodobenzonitrile. $^1$H NMR (DMSO-d6) δ 1.71 (m, 4H), 2.04 (m, 2H), 4.06 (m, 2H), 7.01 (m, 1H), 7.28 (m, 2H), 7.41 (m, 1H), 7.90 (bds, 4H), 8.70 (s, 1H), 10.42 (s, 1H). MS (FAB) 311 (M+H$^+$, 60), 185 (100). Anal. Calcd for $C_{18}H_{18}N_2O_3 \cdot 2H_2O$: C, 62.42; H, 6.40; N, 8.09. Found: C, 62.47; H, 5.33; N, 7.60.

EXAMPLE 15

Preparation of 4-[3-(4-fluorophenyl)phenoxy]butanohydroxamic acid

Step 1: 4-(3-iodophenoxy)butanoic acid.

The desired compound was prepared according to the method of Example 1, steps 1 and 2, except substituting 3-iodophenol for 4-phenylphenol.

Step 2: O-benzyl-4-(3-iodophenoxy)butanohydroxamic acid.

To a solution in dichloromethane (20 mL) containing a few drops of DMF of 4-(3-iodophenoxy)butanoic acid (2.26 g, 7.38 mmol) was added oxalyl chloride (0.60 mL, 6.9 mmol) slowly via syringe. The reaction mixture was stirred for 30 minutes at ambient temperature, and then was decanted into a dichloromethane solution of O-benzylhydroxylamine (3.5 g, 22 mmol; prepared by shaking O-benzylhydroxylamine in a mixture of dichloromethane and saturated aqueous Na$_2$CO$_3$, separating the layers, and drying the organic phase over MgSO$_4$). The reaction mixture was stirred for 3.5 hours at ambient temperature and then was extracted with water and saturated aqueous Na$_2$CO$_3$. The organic phase was dried over MgSO$_4$, filtered, and concentrated in vacuo to give a white solid. The solid was dissolved in dichloromethane and the organic solution was washed with aqueous 1M HCl, dried over MgSO$_4$, filtered, and concentrated in vacuo to give O-benzyl-4-(3-iodophenoxy)butanohydroxamic acid (3.12 g) as a fluffy white solid.

Step 3: O-benzyl-4-[3-(4-fluorophenyl)phenoxy]butanohydroxamic acid.

The desired compound was prepared according to the method of Example 9, step 1, except substituting O-benzyl-4-(3-iodophenoxy)butanohydroxamic acid, prepared as in step 2, for 4-(4-iodophenoxy)butanoic acid ethyl ester and substituting toluene for DME.

Step 4: 4-[3-(4-fluorophenyl)phenoxy]butanohydroxamic acid

To a solution in THF (15 mL) of O-benzyl-4-[3-(4-fluorophenyl)phenoxy]butanohydroxamic acid (0.29 g, 0.77 mmol), prepared as in step 3, was added 10% palladium on carbon (0.107 g) and the mixture was stirred overnight under a positive H$_2$ pressure. Purification by reverse phase high performance liquid chromatography gave 4-[3-(4-fluorophenyl)phenoxy]butanohydroxamic acid (57 mg) as a white solid. $^1$H NMR (DMSO-d6) δ 1.94 (m, 2H), 2.16 (t, 2H, J=7 Hz), 4.03 (t, 2H, J=6 Hz), 6.92 (dd, 1H, J=2, 8 Hz), 7.16 (m, 1H), 7.20 (d, 1H, J=7 Hz), 7.28 (t, 2H, J=9 Hz), 7.37 (t, 1H, J=8 Hz), 7.71 (dd, 2H, J=5, 8 Hz), 8.71 (s, 1H), 10.42 (s, 1H). MS (DCI/NH$_3$) 307 (M+NH$_4^+$, 100), 290 (M+H$^+$, 30). Anal. Calcd for: $C_{16}H_{16}FNO_3$: C, 66.43; H, 5.57; N, 4.84. Found: C, 66.04; H, 5.48; N, 4.78.

EXAMPLE 16

Preparation of 4-[3-(4-cyanophenyl)phenoxy]butanohydroxamic acid

Step 1: O-benzyl -4-[3-(4-cyanophenyl)phenoxy]butanohydroxamic acid.

The desired compound was prepared according to the method of Example 4, steps 2 and 3, except substituting O-benzyl-4-(3-iodophenoxy)butanohydroxamic acid, prepared as in Example 15, step 2, for 4-(4-iodophenoxy)butanoic acid ethyl ester, and substituting 4-bromobenzonitrile for 3-iodobenzonitrile.

Step 2: 4-[3-(4-cyanophenyl)phenoxy]butanohydroxamic acid.

The desired compound was prepared according to the method of Example 15, step 4, except substituting O-benzyl-4-[3-(4-cyanophenyl)phenoxy]butanohydroxamic acid, prepared as in step 1, for N-benzyloxy-4-[3-(4-fluorophenyl)phenoxy]butyramide. $^1$H NMR (DMSO-d6) δ 1.97 (m, 2H), 2.15 (t, 2H, J=7.3 Hz), 4.05 (t, 2H, J=6.2 Hz), 7.01 (m, 1H), 7.29 (m, 2H), 7.42 (t, 1H, J=8.1 Hz), 7.91 (m, 4H), 8.72 (s, 1H), 10.42 (s, 1H). MS (FAB(+)) 297 (M+H$^+$, 95), 264 (80), 102 (100); (FAB(−)) 295 (M−H$^-$, 20), 194 (100). Anal. Calcd for $C_{17}H_{16}N_3O_3$: C, 68.91; H, 5.44; N, 9.45. Found: C, 57.96; H, 4.66; N, 7.41.

EXAMPLE 17

Preparation of 4-[3-(3-cyanophenyl)phenoxy]butanohydroxamic acid

The desired compound was prepared according to the method of Example 16, except substituting 3-bromobenzonitrile for 4-bromobenzonitrile. $^1$H NMR (DMSO-d6) δ 1.97 (m, 2H), 2.15 (t, 2H, J=7.3 Hz), 4.06 (t, 2H, J=6.5 Hz), 6.99 (m, 1H), 7.29 (s, 1H), 7.31 (d, 1H, J=7.7 Hz), 7.40 (t, 1H, J=7.8 Hz), 7.66 (t, 1H, J=7.8 Hz), 7.83 (d, 1H, J=7.7 Hz), 8.03 (d, 1H, J=8.1 Hz), 8.18 (s, 1H), 8.81 (s, 1H), 10.43 (s, 1H). MS (FAB(+)) 319 (M+Na⁺, 10), 297 (M+H⁺, 70), 185 (100); (FAB(−)) 295 (M−H⁻, 25), 194 (100). Anal. Calcd for $C_{17}H_{16}N_3O_3$: C, 68.91; H, 5.44; N, 9.45. Found: C, 59.61; H, 4.94; N, 7.70.

EXAMPLE 18

Preparation of 5-[3-phenylphenoxy] pentanohydroxamic acid

Step 1: 5-(3-phenylphenoxy)pentanoic acid methyl ester.

The desired compound was prepared according to the method of Example 1, step 1, except substituting 3-phenylphenol for 4-phenylphenol, and substituting methyl 5-bromovalerate for ethyl 4-bromobutyrate.

Step 2: 5-(3-phenylphenoxy)pentanoic acid.

To a solution in methanol (7.5 mL) of 5-(3-phenylphenoxy)pentanoic acid methyl ester (1.42 g, 5.0 mmol), prepared as in step 1, was added water (3.75 mL) and aqueous 4N sodium hydroxide (3.75 mL). The reaction mixture was stirred for 3.5 hours and then was concentrated in vacuo. The residue was partitioned between water and ethyl ether. The aqueous phase was taken to pH 2 with concentrated HCl and extracted twice with ethyl acetate. The combined ethyl acetate extracts were dried over $Na_2SO_4$, filtered, and concentrated in vacuo to give a white solid. Trituration of the solid with 1:1 ethyl ether-hexanes gave 5-(3-phenylphenoxy)pentanoic acid (1.21 g) as a white powder.

Step 3: 5-[3-phenylphenoxy]pentanohydroxamic acid.

To a solution in dichloromethane (10 mL) and DMF (10 drops) of 5-(3-phenylphenoxy)pentanoic acid (0.541 g, 2.0 mmol), prepared as in step 2, was added oxalyl chloride (192 µL, 2.2 mmol) over 3 minutes and the yellow solution was stirred for 3 hours and then was cooled in an ice-water bath. A solution in aqueous THF (2.0 mL THF, 0.2 mL $H_2O$) of hydroxylamine (4.0 mmol; prepared by adding triethylamine to a 0° C. solution in aqueous THF of hydroxylamine hydrochloride) was added and the reaction mixture was stirred for 5 minutes in the ice bath and then warmed to ambient temperature for 3 hours. The reaction mixture was concentrated in vacuo and the residue was partitioned between ether and aqueous 1N NaOH. The aqueous phase was extracted twice with dichloromethane. The combined organic layers were concentrated in vacuo to give a yellow oil (507 mg). Chromatography on silica gel (1%, then 5% methanol/dichloromethane), then reverse phase high performance liquid chromatography (gradient from 30% to 95% acetonitrile/water) and trituration with ethyl ether gave 5-[3- and 4-phenylphenoxy]pentanohydroxamic acid (29 mg) as a 83:17 mixture. mp 113.1°–118.0° C. ¹H NMR (DMSO-d6) δ 1.58–1.80 (c, 4H), 1.99–2.08 (c, 2H), 3.98–4.09 (c, 2H), 6.90–6.96 (c, 0.83H), 6.99–7.04 (c, 0.17H), 7.15–7.24 (c, 2H), 7.33–7.40 (c, 2H), 7.42–7.52 (c, 3H), 7.57– 7.63 (c, 0.34H), 7.64–7.70 (c, 1.66H), 8.66 (s, 1H), 10.35 (s, 1H). IR (KBr) 3200, 3040, 2960, 1630, 1600, 1520, 1480, 1470, 1420, 1300, 1290, 1220, 1070, 980, 780, 700 cm⁻¹. MS (DCI/NH₃) 269 (M−16), 286 (M+H)⁺, 303 (M+NH₄)⁺.

EXAMPLE 19

Preparation of 5-[4-phenylphenoxy] pentanohydroxamic acid

Step 1: 5-(4-phenylphenoxy)pentanoic acid methyl ester.

A mixture in acetone of 4-phenylphenol (0.85 g, 5.0 mmol) and potassium carbonate (0.76 g, 5.5 mmol) was stirred for 30 minutes. Neat methyl 5-bromovalerate (0.78 mL, 5.5 mmol) was added dropwise via syringe and the reaction mixture was stirred for 2 hours at ambient temperature and overnight at reflux. Catalytic KI was then added and the reaction mixture was heated overnight at reflux. An additional 10 drops of methyl 5-bromovalerate was then added and reflux was continued for 8 hours. The reaction mixture was cooled to ambient temperature and filtered. The collected solid was washed with acetone and the combined filtrate and washings were concentrated in vacuo. The residue was partitioned between ethyl ether and water. The aqueous phase was extracted with ethyl ether. The combined organic layers were dried over $Na_2SO_4$, filtered, and concentrated in vacuo to give 5-(4-phenylphenoxy)pentanoic acid methyl ester (1.66 g) as a white powder.

Step 2: 5-[4-phenylphenoxy]pentanohydroxamic acid.

The desired compound was prepared according to the method of Example 18, steps 2 and 3, except substituting 5-(4-phenylphenoxy)pentanoic acid methyl ester, prepared as in step 1, for 5-(3-phenylphenoxy)pentanoic acid methyl ester. mp 151.5°–153.5° C. ¹H NMR(DMSO-d6) δ 10.36 (S, 1H), 8.66 (d, 1H, J=1.5 Hz), 7.65–7.55 (c, 4H), 7.46–7.39 (c, 2H), 7.34–7.26 (c, 2H), 4.00 (t, 2H, J=6 Hz), 2.03 (t, 2H, J=6 Hz), 1.80–1.58 (c, 4H). IR (KBr) 3200, 3040, 2920, 2860, 1660, 1640, 1620, 1610, 1520, 1490, 1470, 1290, 1270, 1250, 1200, 1180, 1030, 840, 780, 690 cm⁻¹. MS (DCI/NH₃) 269 (M−16), 286 (M+H)⁺, 303 (M+NH₄)⁺. Anal. Calcd for: $C_{17}H_{19}NO_3 \cdot 0.25 H_2O$: C, 70.44; H, 6.78; N, 4.83. Found: C, 70.71; H, 6.82; N, 4.98.

EXAMPLE 20

Preparation of 5-[4-(4-cyanophenyl)phenoxy] pentanohydroxamic acid

Step 1: 5-(4-(4-cyanophenyl)phenoxy)pentanoic acid.

The desired compound was prepared according to the method of Example 2, steps 1 and 2, except substituting 4'-hydroxy-4-biphenylcarbonitrile for 3-phenylphenol.

Step 2: 5-[4-(4-cyanophenyl)phenoxy]pentanohydroxamic acid.

To a solution in THF (13 mL) of 5-(4-(4-cyanophenyl) phenoxy)pentanoic acid (0.50 g, 1.7 mmol), prepared as in step 1, was added DMF (10 µL, 0.13 mmol), and oxalyl chloride (0.16 mL, 1.9 mmol) and the reaction mixture was stirred for 2 hours. A solution in THF (2 mL) of O-tert-butyldimethylsilylhydroxylamine (0.30 g, 2.0 mmol) and triethylamine (0.25 mL, 1.8 mmol) was added dropwise via syringe and the reaction mixture was stirred for 3.5 hours. The reaction mixture was quenched with methanol and concentrated in vacuo. The residue was partitioned between aqueous 1M NaOH and ethyl ether, and the aqueous phase was extracted with ethyl ether. The aqueous phase was taken to pH 2 with concentrated HCl and extracted three times with dichloromethane. The combined dichloromethane extracts were dried over $Na_2SO_4$, filtered, and concentrated in vacuo to give a white solid. Recrystallization from ethyl acetate gave 5-[4-(4-cyanophenyl)phenoxy] pentanohydroxamic acid (0.24 g) as a white solid. mp 141.8°–142.6° C. ¹H NMR (DMSO-d6) δ 1.59–1.84 (c, 4H), 2.03 (t, 2H, J=7.5 Hz), 4.03 (t, 2H, J=6 Hz), 7.06 (d, 2H, J=9 Hz), 7.69 (s, 1H), 7.72 (s, 1H), 7.81–7.92 (c, 4H), 8.71 (s, 1H), 10.39 (s, 1H). IR (KBr) 3200, 3030, 3010, 2860, 2240, 1630, 1600, 1540, 1520, 1490, 1470, 1460, 1390, 1290, 1250, 1180, 1110, 980, 850, 820, 630, 580, 530 cm⁻¹. MS (DCI/NH₃) 294 (M−16), 311 (M+H)⁺, 328 (M+NH₄)⁺. Anal. Calcd for $C_{18}H_{18}N_2O_3$: C, 69.66; H, 5.85; N, 9.03. Found: C, 69.54; H, 5.73; N, 8.99.

EXAMPLE 21

Preparation of 6-[4-phenylphenoxy] hexanohydroxamic acid

The desired compound was prepared according to the method of Example 20, except substituting 4-phenylphenol for 4'-hydroxy-4-biphenylcarbonitrile, and substituting ethyl 6-bromohexanoate for methyl 5-bromovalerate. mp 151.1°–151.8° C. $^1$H NMR (DMSO-d6) δ 1.34–1.49 (c, 2H), 1.57 (m, 2H, J=7.5 Hz), 1.73 (m, 2H, J=7.5 Hz), 1.98 (t, 2H, J=7.5 Hz), 3.99 (t, 2H, J=7.5 Hz), 6.99 (s, 1H), 7.02 (s, 1H), 7.16–7.25 (c, 1H), 7.42 (t, 2H, J=7.5 Hz), 7.54–7.65 (c, 4H), 8.65 (s, 1H, 10.33 (s, 1H) IR (KBr) 3280, 3060, 3040, 2960, 2860, 1660, 1610, 1520, 1490, 1470, 1450, 1400, 1280, 1270, 1250, 1200, 1080, 1040, 830, 780, 690 cm$^{-1}$. MS (DCI/NH$_3$) 283 (M+H)$^+$, 317 (M+NH$_4$)$^+$. Anal. Calcd for C$_{18}$H$_{21}$NO$_3$: C, 72.21; H, 7.07; N, 4.68. Found: C, 71.85; H, 7.29; N, 4.65.

EXAMPLE 22

Preparation of 6-[4-(4-cyanophenyl)phenoxy] hexanohydroxamic acid

The desired compound was prepared according to the method of Example 21, except substituting 4'-hydroxy-4-biphenylcarbonitrile for 4-phenylphenol. mp 129.4°–131.4.° C. $^1$H NMR(DMSO-d6) δ 1.33–1.48 (c, 2H), 1.57 (m, 2H, J=7.5 Hz), 1.73 (m, 2H, J=7.5 Hz), 1.99 (t, 2H, J=7.5 Hz), 4.02 (t, 2H, J=6 Hz), 7.05 (d, 2H, J=12 Hz), 7.68 (s, 1H, 7.71 (s, 1H, 7.80–7.91 (c, 4H). IR (KBr) 3300, 3050, 2950, 2850, 2200, 1660, 1600, 1560, 1530, 1500, 1470, 1400, 1275, 1250, 1170, 1120, 1090, 1050, 1000, 840, 830, 570, 550 cm$^{-1}$. MS (DCI/NH$_3$) 308(M−16), 325 (M+H)$^+$, 342 (M+NH$_4$)$^+$. Anal. Calcd for C$_{19}$H$_{20}$N$_2$O$_3$·0.25 H$_2$O: C, 69.38; H, 6.28; N, 8.52. Found: C, 69.61; H, 6.11; N, 8.18.

EXAMPLE 23

Preparation of 3-(4-phenylphenoxy) propanohydroxamic acid

Step 1: 3-(4-phenylphenoxy)propionic acid.

To a solution in THF of 4-phenylphenol (1.86 g, 10.9 mmol) was added potassium tert-butoxide (1.22 g, 10.9 mmol). Neat β-propiolactone (0.68 mL, 10.9 mmol) was added dropwise. The resulting white suspension was stirred overnight at ambient temperature and then was concentrated in vacuo. The residue was partitioned between ethyl acetate and saturated aqueous NaHCO$_3$. The organic phase was discarded and the aqueous phase was acidified and extracted twice with ethyl acetate. The ethyl acetate extracts were combined, dried over MgSO$_4$, filtered, and concentrated in vacuo to give 3-(4-phenylphenoxy)propionic acid (0.86 g) as a white solid.

Step 2: 3-(4-phenylphenoxy)propanohydroxamic acid.

The desired compound was prepared according to the method of Example 1, step 3, except substituting 3-(4-phenylphenoxy)propionic acid, prepared as in step 1, for 3-(4-phenylphenoxy)butanoic acid. $^1$H NMR (DMSO-d6) δ 2.44 (t, 2H, J=7 Hz), 4.22 (t, 2H, J=7 Hz), 7.01 (d, 2H, J=6 Hz), 7.31 (t, 1H, J=5 Hz), 7.42 (t, 2H, J=5 Hz), 7.61 (m, 4H), 8.88 (bds, 1H, 10.53 (s, 1H). MS (DCI/NH$_3$) 275 (M+NH4$^+$, 100). Anal. Calcd for C$_{15}$H$_{15}$NO$_3$·0.25 H$_2$O: C, 68.82; H, 5.36; N, 5.70. Found: C, 68.78; H, 5.27; N, 5.18.

EXAMPLE 24

Preparation of 3-(3-phenylphenoxy) propanohydroxamic acid

Step 1: 3-(3-phenylphenoxy)propionic acid.

The desired compound was prepared according to the method of Example 23, step 1, except substituting 3-phenylphenol for 4-phenylphenol.

Step 2: 3-(3-phenylphenoxy)propanohydroxamic acid.

A mixture of 3-(3-phenylphenoxy)propionic acid (0.27 g, 1.1 mmol) and excess thionyl chloride was heated at reflux for 30 minutes. The mixture was cooled to ambient temperature and concentrated in vacuo. The residue was azeotroped three times with ethyl ether, and then was taken up in THF (30 mL). To the acid chloride solution was added aqueous hydroxylamine (3.34 mmol; prepared by adding 2.8 mL of aqueous 50% NaOH to a solution in 5 mL water of hydroxylamine hydrochloride) and the reaction mixture was stirred for 4 hours. The reaction mixture was quenched with 1:1 dichloromethane-saturated aqueous NH$_4$Cl. The aqueous phase was washed with brine, dried over Na$_2$SO$_4$, filtered, and concentrated in vacuo. The residue was taken up in ethyl ether and left standing at −30° C. for 3 days. The resulting crystals were collected to give 3-(3-phenylphenoxy)propanohydroxamic acid. mp 113°–116° C. $^1$H NMR (DMSO-d6) δ 10.58 (s, 1H), 8.68–8.63 (d, 1H, J=1.5 Hz), 7.67–7.65 (d, 2H, J=7 Hz), 7.48–7.43 (t, 2H, J=7.7 Hz), 7.38–7.34 (t, 2H, J=7.7 Hz), 7.24–7.21 (d, 1H, J=7.4 Hz), 7.15 (m, 1H), 6.94–6.90 (dd, 1H, J=3, 7 Hz), 4.28–4.24 (t, 2H, J=6 Hz), 2.47–2.43 (t, 2H, J=6 Hz). MS (DCI/NH$_3$) 275 (M+NH$_4$)$^+$. Anal. Calcd for C$_{15}$H$_{15}$NO$_3$·0.25H$_2$O: C, 68.82; H, 55.96; N, 5.35. Found: C, 68.92; H, 5.87; N, 5.33.

EXAMPLE 25

Preparation of 3-[4-(4-cyanophenyl)phenoxy] propanohydroxamic acid

The desired compound was prepared according to the method of Example 23, except substituting 4'-hydroxy-4-biphenylcarbonitrile for 3-phenylphenol, and using a THF-DMF solvent mixture. mp 114°–118° C. $^1$H NMR (DMSO-d6) δ 2.45 (t, 2H, J=5.9 Hz), 4.25 (t, 2H, J=5.9 Hz), 7.06 (d, 2H, J=8.8 Hz), 7.72 (d, 2H, J=8.8 Hz), 7.85 (d, 2H, J=8.5 Hz), 7.88 (d, 2H, J=8.5 Hz), 8.87 (s, 1H), 10.56 (s, 1H). IR (microscope) 3241 (br), 2244 (w), 2235 (w), 1629 (s), 1606 (m), 1496 (m), 1257 (m), 815 (m) cm$^{-1}$. MS (DCI/NH$_3$) 300 (M+NH$_4$)$^+$, 317 (M+NH$_4$+NH$_3$)$^+$. Anal. Calcd for C$_{16}$H$_{14}$N$_2$O$_3$·0.60 H$_2$O: C, 65.56; H, 5.23; N, 9.56. Found: C, 65.41; H, 4.85; N, 9.83.

EXAMPLE 26

Preparation of 3-[4-(4-methoxyphenyl)phenoxy] propanohydroxamic acid

The desired compound was prepared according to the method of Example 24, except substituting 4-hydroxy-4'-methoxybiphenyl for 3-phenylphenol, and using a THF-DMF solvent mixture for the lactone opening. $^1$H NMR (DMSO-d6) δ 2.44 (t, 2H, J=6.1 Hz), 3.78 (s, 3H), 4.21 (t, 2H, J=6.1 Hz), 6.96 (d, 2H, J=8.8 Hz), 6.98 (d, 2H, J=8.8 Hz), 7.52 (d, 2H, J=8.8 Hz), 7.54 (d, 2H, J=8.8 Hz), 8.83 (s, 1H), 10.52 (s, 1H). IR (microscope) 3279 (br), 2948 (w), 1629 (s), 1503 (m), 1470 (m), 1275 (s), 1250 (m), 1052 (m), 815 (s) cm$^{-1}$. MS (DCI/NH$_3$) 305 (M+NH$_4$)$^+$. Anal. Calcd for C$_{16}$H$_{17}$NO$_4$·0.25 H$_2$O: C, 65.85; H, 6.04; N, 4.79. Found: C, 65.80; H, 5.83; N, 4.50.

EXAMPLE 27

Preparation of 3-[4-(4-fluorophenyl)phenoxy] propanohydroxamic acid

Step 1: 4-(4-fluorophenyl)phenol.

A mixture under N$_2$ in DMF (18 mL) of 4-iodophenol (2.00 g, 9.09 mmol), 4-fluorophenylboronic acid (1.40 g, 10.0 mmol), cesium carbonate (4.44 g, 13.6 mmol), and tetrakis(triphenylphosphine)palladium(0) (0.27 g, 0.23 mmol) was stirred for 10 minutes at ambient temperature and then overnight at reflux. The reaction mixture was cooled to ambient temperature, diluted with ethyl acetate, and extracted twice with water. The organic phase was washed with brine, dried over $Na_2SO_4$, filtered, and concentrated in vacuo. Chromatography on silica gel (10:1, then 5:1 hexanes-ethyl acetate) gave 4-(4-fluorophenyl)phenol (0.79 g, 46%) as a white powder.

Step 2: 3-[4-(4-fluorophenyl)phenoxy]propanohydroxamic acid.

The desired compound was prepared according to the method of Example 26, except substituting 4-(4-fluorophenyl)phenol, prepared as in step 1, for 3-phenylphenol. $^1$H NMR (DMSO-d6) δ 2.44 (t, 2H, J=6.0 Hz), 4.22 (t, 2H, J=6.0 Hz), 7.00 (d, 2H, J=8.8 Hz), 7.25 (t, 2H, J (F-Hortho, Hortho-Hmeta)=9.0 Hz), 7.56 (d, 2H, J=8.5 Hz), 7.64 (dd, 2H, J (F-Hmeta, Hortho-Hmeta)=5.4, 8.8 Hz), 8.83 (d, 1H, J=1.7 Hz), 10.52 (d, 1H, J=1.4 Hz). IR (Microscope) 3146 (br), 3022 (br), 2920 (m), 1659 (s), 1626 (s), 1501 (s), 1288 (m), 1248 (s), 816 (s) cm$^{-1}$. MS (DCI/$NH_3$) 293 (M+$NH_4$)$^+$. Anal. Calcd for $C_{15}H_{14}NO_3F$: C, 65.44; H, 5.12; N, 5.08. Found: C, 65.21; H, 5.13; N, 4.83.

EXAMPLE 28

Preparation of (S)2-methyl-3-(4-phenylphenoxy)propanohydroxamic acid

Step 1: tris(4-biphenyl)bismuth.

To a −78° C. solution in THF (325 mL) of 4-bromobiphenyl (7.51 g, 32.5 mmol) was added tert-butyllithium (1.7M, 38 mL, 64.6 mmol) and the dark-green solution was stirred for 15 minutes. A solution in THF (30 mL) of bismuth trichloride (3.38 g, 10.7 mmol) was added via syringe, and the reaction mixture was warmed to ambient temperature over 3 hours. The reaction mixture was quenched with saturated aqueous $NH_4Cl$ and extracted with ethyl acetate. The organic phase was dried over $MgSO_4$, filtered, and concentrated in vacuo to give tris(4-biphenyl)bismuth (6.53 g) as a yellow solid.

Step 2: (S)2-methyl-3-(4-phenylphenoxy)propionic acid methyl ester.

To a suspension in 4:1 dichloromethane-THF (30 mL) of tris(4-biphenyl)bismuth (1.96 g, 2.93 mmol) was added peracetic acid (32% in aqueous acetic acid, 0.73 g, 3.1 mmol). After 30 seconds, methyl (S)-(+)-3-hydroxy-2-methylpropionate (0.355 g, 3.00 mmol) and copper(II) acetate (0.515 g, 2.84 mmol) were rinsed into the reaction flask with 4:1 dichloromethane-THF (10 mL). The reaction mixture was heated at reflux for 20 hours, then was cooled to ambient temperature and quenched with saturated aqueous $NaHSO_3$ solution. The mixture was partitioned between dichloromethane and pH 7 buffer. The organic phase was dried over $Na_2SO_4$, filtered, and concentrated in vacuo to give a yellow brown solid (1.35 g). Chromatography on silica gel (3:1, then 2:1, then 1:1 hexanes-dichloromethane, then dichloromethane) gave (S)2-methyl-3-(4-phenylphenoxy)propionic acid methyl ester (0.062 g) as a pale yellow solid.

Step 4: (S)2-methyl-3-(4-phenylphenoxy)propionic acid.

To a solution in THF (4 mL) of (S)2-methyl-3-(4-phenylphenoxy)propionic acid methyl ester (0.14 g, 0.52 mmol), prepared as in step 2, was added aqueous lithium peroxide (1.1 mmol; prepared by adding 0.047 g of lithium hydroxide hydrate to 0.135 g of 30% aqueous $H_2O_2$ in 2 mL of $H_2O$) and THF (4 mL). The reaction mixture was stirred for 7 hours and then was quenched with aqueous $NaHSO_3$, taken to pH9 with saturated aqueous $Na_2CO_3$, and extracted with ethyl ether. The aqueous phase was taken to pH 2 with HCl and extracted twice with ethyl acetate. The combined ethyl acetate extracts were dried over $Na_2SO_4$, filtered, and concentrated in vacuo to give (S)2-methyl-3-(4-phenylphenoxy)propionic acid (61 mg) as a white solid.

Step 3: (S)2-methyl-3-(4-phenylphenoxy)propanohydroxamic acid.

The desired compound was prepared according to the method of Example 1, step 3, except substituting (S)2-methyl-3-(4-phenylphenoxy)propionic acid, prepared as in step 2, for 4-(3-phenylphenoxy)butanoic acid. mp 187°–188° C. $^1$H NMR (DMSO-d6) δ 1.09 (d, 3H, J=7 Hz), 2.62 (m, 1H), 3.90 (dd, 1H, J=5, 9 Hz), 4.13 (t, 1H, J=9 Hz), 7.00 (d, 2H, J=9 Hz), 7.31 (m, 1H), 7.42 (t, 2H, J=8 Hz), 7.59 (m, 4H), 8.83 (d, 1H, J=2 Hz), 10.56 (d, 1H, J=2 Hz). MS (DCI/$NH_3$) 289 (M+$NH_4^+$, 100). Anal. Calcd for $C_{16}H_{17}NO_3$: C, 70.83; H, 6.32; N, 5.16. Found: C, 70.57; H, 6.22; N, 4.82.

EXAMPLE 29

Preparation of 3-(N-methylcarboxamido)-5-[4-(4-cyanophenyl)phenoxy]pentanohydroxamic acid Step 1: 4-[4-(4-cyanophenyl)phenoxy]butanoic acid ethyl ester.

The desired compound was prepared according to the method of Example 1, step 1, except substituting 4'-hydroxy-4-biphenylcarbonitrile for 4-phenylphenol.

Step 2: 3-carboethoxy-5-[4-(4-cyanophenyl)phenoxy]pentanoic acid tert-butyl ester.

To a −78° C. solution in THF (100 mL) of diisopropylamine (0.94 mL, 7.15 mmol) was added n-butyllithium (2.5M in hexanes, 2.86 mL, 7. 15 mmol) and the mixture was stirred for 15 minutes. A solution in THF (25 mL) of 4-[4-(4-cyanophenyl)phenoxy]butanoic acid ethyl ester (2.01 g, 6.5 mmol), prepared as in step 1, was added dropwise and the reaction mixture was stirred for 15 minutes. Neat t-butyl bromoacetate (1.03 mL, 6.8 mmol) was added rapidly and the reaction mixture was stirred at −78° C. for 2 hours, then for 0.5 hours at ambient temperature. The reaction mixture was quenched with saturated aqueous $NH_4Cl$ and extracted twice with ethyl ether. The combined organic layers were dried over $MgSO_4$, filtered, and concentrated in vacuo. Successive chromatographies on silica gel (dichloromethane, then 1:3 ethyl acetate-hexanes) gave 3-carboethoxy-5-[4(4-cyanophenyl)phenoxy]pentanoic acid tert-butyl ester (0.91 g, 33%).

Step 3: 3-carboxy-5-[4-(4-cyanophenyl)phenoxy]pentanoic acid tert-butyl ester.

To a solution in 2-propanol (30 mL) of 4-carboethoxy-5-[4-(4-cyanophenyl)phenoxy]pentanoic acid tert-butyl ester (0.9 g), prepared in step 1, was added aqueous 1M lithium hydroxide (8.6 mmol) and water (5 mL) to form a clear solution, and the reaction mixture was stirred for 3 hours. The reaction mixture was quenched with saturated aqueous $NH_4Cl$ and extracted twice with ethyl ether and once with ethyl acetate. The combined organic layers were dried over $MgSO_4$, filtered, and concentrated in vacuo. Chromatography on silica gel (4% methanol-dichloromethane) provided 3-carboxy-5-[4-(4-cyanophenyl)phenoxy]pentanoic acid tert-butyl ester (0.62 g).

Step 4. 3-(N-methylcarboxamido)-5-[4-(4-cyanophenyl)phenoxy]pentanoic acid tert-butyl ester.

To a solution in dry dichloromethane (100 mL) of 4-carboxy-5-[4-(4-cyanophenyl)phenoxy]pentanoic acid tert-butyl ester (0.62 g, 1.57 mmol) was added methylamine hydrochloride (0.159 g, 2.35 mmol) and 4-methylmorpholine (0.26 mL, 2.35 mmol). The reaction mixture was cooled to 0° C. and 1-(3-dimethylaminopropyl)-3-ethylcarbodiimide hydrochloride (0.361 g, 1.88 mmol) was added. The reaction mixture was warmed slowly to ambient temperature and stirred overnight. The reaction mixture was extracted with aqueous 1N HCl, twice with dichloromethane, and once with ethyl acetate. The combined organic layers were dried over $MgSO_4$, filtered, and concentrated in vacuo. Chromatography on silica gel (4% methanol-dichloromethane) provided 3-(N-methylcarboxamido)-5-[4-(4-cyanophenyl)phenoxy] pentanoic acid tert-butyl ester (0.24 g).

Step 5: 3-(N-methylcarboxamido)-5-[4-(4-cyanophenyl) phenoxy]pentanoic acid.

A mixture of 3-(N-methylcarboxamido)-5-[4-(4-cyanophenyl)phenoxy]pentanoic acid tert-butyl ester (0.22 g), prepared as in step 4, and trifluoroacetic acid (1.0 mL) was placed in the sonic bath until all of the solid dissolved and then was stirred for 15 minutes at ambient temperature. The reaction mixture was concentrated in vacuo and the residue was azeotroped with dichloromethane and ethyl ether to give 3-(N-methylcarboxamido)-5-[4-(4-cyanophenyl)phenoxy]pentanoic acid (0.22 g).

Step 6: 3-(N-methylcarboxamido)-5-[4-(4-cyanophenyl) phenoxy]pentanohydroxamic acid The desired compound was prepared according to the method of Example 29, step 5, except substituting 3-(N-methylcarboxamido)-5-[4-(4-cyanophenyl)phenoxy] pentanoic acid, prepared as in step 5, for 3-methyl-2-[4-(4-cyanophenyl)phenoxy]butanoic acid. mp 176° C. $^1H$ NMR (DMSO-D6) δ 1.75–1.97 (m, 2H), 2.11 (dd, 1H, J=7.5, 7.5 Hz), 2.26 (dd, 1H, J=7.5, 7.5 Hz), 2.56 (d, 3H, J=4.5 Hz), 2.77–2.88 (m, 1H), 3.90–4.01 (m, 2H), 7.02 (d, 2H, J=9 Hz), 7.71 (d, 2H, J=9 Hz), 7.81–7.91 (m, 5H), 8.75 (s, 1H), 10.42 (s, 1H). MS (DCI/NH$_3$) 368 (M+H)$^+$, 352. Anal. Calcd for $C_{20}H_{21}N_3O_4 \cdot 0.25$ $H_2O$: C, 64.59; H, 5.82; N, 11.29. Found: C, 64.51; H, 5.62; N, 11.15.

EXAMPLE 30

Preparation of 3-(4-biphenylthio) propanohydroxamic acid

Step 1: 2-(4-bromophenylthio)propanoic acid.

The desired compound was prepared according to the method of Example 23, step 1, except substituting 4-bromothiophenol for 4-phenylphenol, and using 10:2 THF-DMF as solvent.

Step 2: O-tert-butyl-3-(4-bromophenylthio) propanohydroxamic acid.

To a solution in THF (100 mL) of 3-(4-bromophenylthio) propanoic acid (6.88 g, 26.5 mmol) was added 4-methylmorpholine (2.94 g, 29.2 mmol) and isobutyl chloroformate (3.6 g, 29.2 mmol) and the reaction mixture was stirred for 1 hour. To the reaction mixture was added aqueous O-tert-butylhydroxylamine (39.8 mmol; prepared by dissolving the hydrochloride in water and adding 3M NaOH to give the free base) and the reaction mixture was stirred overnignt at ambient temperature. The reaction mixture was poured into a mixture of ethyl ether and saturated aqueous $NH_4Cl$. The aqueous phase was extracted with ethyl ether. The combined organic layers were washed with brine, dried over $MgSO_4$, filtered, and concentrated in vacuo. Chromatography on silica gel (30% ethyl acetate-hexanes) gave O-tert-butyl-2-(4-bromophenylthio) propanohydroxamic acid (5.36 g, 60%).

Step 3: O-tert-butyl-2-(4-biphenylphenylthio) propanohydroxamic acid.

The desired compound was prepared according to the method of Example 9, step 1, except substituting N-tert-butoxy-2-(4-bromophenylthio)propanohydroxamic acid, prepared as in step 2, for 4-(4-iodophenoxy)butyric acid ethyl ester.

Step 4: 2-(4-biphenylthio)propanohydroxamic acid.

To a 0° C. solution in dichloromethane (2 mL) of N-tert-butoxy-2-(4-biphenylphenylthio)propanohydroxamic acid (0.27 g, 0.82 mmol), prepared as in step 3, was added trifluoroacetic acid (10 mL), and the reaction mixture was warmed slowly to ambient temperature and stirred overnight. The reaction mixture was concentrated in vacuo. Trituration of the residue with acetonitrile containing 1% trifluoroacetic acid gave 2-(4-biphenylthio) propanohydroxamic acid (113 mg) as a white solid. mp 156°–158° C. $^1H$ NMR (DMSO-d6) δ 10.47 (s,. 1H), 7.67–7.62 (m, 4H), 7.48–7.33 (m, 5H), 3.21–3.17 (t, 2H, J=7 Hz), 2.32–2.31 (t, 2H, J=7.4 Hz). MS (DCI/NH$_3$) 291 (M+NH$_4$)$^+$. Anal. Calcd for $C_{15}H_{15}NO_2S$: C, 65.91; H, 5.53; N, 5.12. Found: C, 65.26; H, 5.52; N, 4.73.

EXAMPLE 31

Preparation of 2-(4-biphenylthio)ethanohydroxamic acid

Step 1: 2-(4-bromophenylthio)ethanoic acid tert-butyl ester.

The desired compound was prepared according to the method of Example 1, step 1, except substituting 4-bromothiophenol for 4-phenylphenol, and substituting tert-butyl bromoacetate for ethyl-4-bromobutyrate.

Step 2: 2-(4-biphenylthio)ethanoic acid tert-butyl ester.

The desired compound was prepared according to the method of Example 9, step 1, except substituting 2-(4-bromophenylthio)ethanoic acid tert-butyl ester, prepared as in step 1, for 4-(4-iodophenoxy)butyric acid ethyl ester.

Step 3: 2-(4-biphenylthio)ethanoic acid.

The desired compound was prepared according to the method of Example 31, step 4, except substituting 2-(4-biphenylthio)ethanoic acid tert-butyl ester, prepared as in step 2, for N-tert-butoxy-2-(4-biphenylphenylthio) propanohydroxamic acid.

Step 4: 2-(4-biphenylthio)ethanohydroxamic acid.

The desired compound was prepared according to the method of Example 31, step 2, except substituting 2-(4-biphenylthio)ethanoic acid, prepared as in step 3, for 3-(4-bromophenylthio)propanoic acid, and substituting aqueous hydroxylmine for aqueous O-tert-butylhydroxylamine. mp 156°–158° C. $^1H$ NMR (DMSO-d6) δ 10.72 (s, 1H), 9.01 (s, 1H), 7.67–7.61 (m, 4H), 7.48–7.43 (m, 4H), 7.38–7.33 (t, 1H, J=8.0 Hz), 3.58 (s, 2H). MS (DCI/NH$_3$) 277 (M+NH$_4$)$^+$.

EXAMPLE 32

Preparation of 3-(4-biphenylamino) propanohydroxamic acid

Step 1: 3-(4-biphenylamino)propanoic acid.

To a solution in THF (30 mL) of 4-aminobiphenyl (2.89 g, 17.1 mmol) was added 1,3-propiolactone (1.60 g, 22.3 mmol), and the reaction mixture was stirred at ambient temperature for 16 hours, at reflux for 5 hours, and at ambient temperature for 48 hours. The reaction mixture was quenched with aqueous 1N sodium carbonate and the THF was evaporated in vacuo. The aqueous solution was extracted twice with ethyl acetate and acidified with concentrated HCl. The acidic mixture was extracted three times with dichloromethane. The combined dichloromethane extracts were dried over $MgSO_4$, filtered, and concentrated in vacuo to give 3-(4-biphenylamino)propanoic acid.

Step 2: 3-(4-biphenylamino)propanohydroxamic acid.

The desired compound was prepared according to the method of Example 31, step 2, except substituting 3-(4-biphenylamino)propanoic acid, prepared as in step 1, for 3-(4-bromophenylthio)propanoic acid, and substituting aqueous hydroxylamine for aqueous O-tert-butylhydroxylamine. 160° C. (dec). $^1H$ NMR (DMSO-d6) δ 7.56–7.53 (d, 2H, J=8.4 Hz), 7.45–7.42 (d, 2H, J=8.1 Hz), 7.40–7.35 (t, 1H, J=7.4 Hz), 7.24–7.21 (t, 1H, J=7.1 Hz), 6.72–6.68 (d, 2H, J=7.2 Hz), 3.31–3.27 (t, 2H, J=7 Hz), 2.29–2.25 (t, 2H, J=7 Hz). MS (DCI/$NH_3$) 257 (M+H)$^+$.

EXAMPLE 33

Preparation of 2-(4-biphenyl)ethanohydroxamic acid

The desired compound was prepared according to the method of Example 1, step 3, except substituting 4-biphenylacetic acid for 4-(4-phenylphenoxy)butanoic acid. mp 200°–201° C. $^1H$ NMR (DMSO-d6) δ 3.37 (s, 2H), 7.36 (m, 3H), 7.46 (t, 2H, J=8 Hz), 7.63 (m, 4H), 8.88 (s, 1H), 10.75 (s, 1H). IR (KBr) 3400 (br), 3200, 3030, 2900, 1625, 1485 cm$^{-1}$. MS (DCI/$NH_3$) 245 (M+$NH_4^+$, 100). Anal. Calcd for $C_{14}H_{13}NO_2 \cdot 0.66 H_2O$: C, 68.44; H, 6.77; N, 6.14. Found: C, 68.55; H, 6.68; N, 5.87.

EXAMPLE 34

Preparation of 4-(4-biphenyl)butanohydroxamic acid

Step 1: N-benzyloxy-4-(4-biphenyl)butyramide.

A suspension of 4-iodophenylbutyric acid (2.0 g, 6.9 mmol) in thionyl chloride (4 mL) was heated at reflux for 20 minutes. The reaction mixture was cooled to ambient temperature, concentrated in vacuo, and the residue was taken up in dichloromethane and decanted into a dichloromethane solution of O-benzylhydroxylamine (26 mmol; prepared by shaking O-benzylhydroxylamine in a mixture of dichloromethane and saturated aqueous $Na_2CO_3$, separating the layers, and drying the organic phase over $MgSO_4$). The reaction mixture was stirred for 3.5 hours at ambient temperature and then was partitioned between dichloromethane and water. The organic phase was washed with aqueous 1M HCl and saturated aqueous sodium carbonate, dried over $MgSO_4$, filtered, and concentrated in vacuo to give N-benzyloxy-4-(4-biphenyl)butyramide (2.47 g) as a tan solid.

Step 2: 4-(4-biphenyl)butanohydroxamic acid.

The desired compound was prepared according to the method of Example 15, steps 3 and 4, except substituting N-benzyloxy-4-(3-iodophenyl)butyramide, prepared as in step 1, for N-benzyloxy-4-(3-iodophenoxy)butyramide. mp 168°–170° C. $^1H$ NMR (DMSO-d6) δ 1.84 (m, 2H), 1.99 (t, 2H, J=7.4 Hz), 2.60 (t, 2H, J=7.7 Hz), 7.28 (d, 2H, J=8.1 Hz), 7.35 (d, 1H, J=7.0 Hz), 7.45 (t, 2H, J=7.4 Hz), 7.58 (d, 2H, J=7.7 Hz), 7.64 (d, 2H, J=7.0 Hz), 8.70 (s, 1H), 10.38 (s, 1H). MS (DCI/$NH_3$) 273 (M+$NH_4^+$, 100), 256 (M+H$^+$, 10). Anal. Calcd for $C_{16}H_{17}NO_2$: C, 75.27; H, 6.72; N, 5.49. Found: C, 75.12; H, 6.72; N, 5.47.

EXAMPLE 35

Preparation of 4-[4-(4-cyanophenyl)phenyl] butanohydroxamic acid

Step 1: N-benzyloxy-4-[4-(4-cyanophenyl)phenyl] butyramide.

The desired compound was prepared according to the method of Example 4, steps 2 and 3, except substituting N-benzyloxy4-(3-iodophenyl)butyramide, prepared as in Example 43, step 1, for 4-(4-iodophenoxy)butanoic acid ethyl ester, and substituting 4-bromobenzonitrile for 3-iodobenzonitrile.

Step 2: 4-[4-(4-cyanophenyl)phenyl]butanohydroxamic acid.

The desired compound was prepared according to the method of Example 15, step 4, except substituting N-benzyloxy-4-[4-(4-cyanophenyl)phenyl]butyramide, prepared as in step 1, for N-benzyloxy-4-[3-(4-fluorophenyl) phenoxy]butyramide. $^1H$ NMR (DMSO-d6) δ 1.82 (m, 2H), 1.99 (t, 2H, J=8 Hz), 2.62 (t, 2H, J=7 Hz), 7.33 (d, 2H, J=9 Hz), 7.69 (d, 2H, J=9 Hz), 7.89 (m, 4H), 8.68 (s, 1H), 10.38 (s, 1H). MS (DCI/$NH_3$) 298 (M+$NH_4^+$, 80), 280 (M+H$^+$, 75), 236 (100).

EXAMPLE 36

Preparation of trans 3-(4-biphenyl) propenohydroxamic acid

To a suspension in dichloromethane of 4-phenylcinnamic acid (2.18 g, 9.75 mmol) was added oxalyl chloride (0.85 mL, 9.8 mmol) and the reaction mixture was stirred for 10 minutes. In a separate flask, hydroxylmine hydrochloride (1.98 g, 8.5 mmol) was dissolved in water (15 mL) and 4-methylmorpholine (3.3 mL, 30 mmol) and THF (30 mL) were added. The solution of hydroxylamine in aqueous THF was then added to the acid chloride solution and the mixture was stirred for 2 hours. The reaction mixture was then shaken with a dichloromethane/saturated aqueous $NH_4Cl$ mixture. The resulting precipitate was filtered off and rinsed with water. The dichloromethane was separated, dried over $MgSO_4$, filtered, and concentrated in vacuo to give trans 3-(4-bipenyl)propenohydroxamic acid (0.78 g) as a peach-colored solid. mp 160°–163° C. $^1H$ NMR(DMSO-d6) δ 6.51 (d, 1H, J=15 Hz), 7.42 (m, 1H), 7.29 (m, 3H), 7.73 (m, 6H), 9.01 (s, 1H), 10.75 (s, 1H). IR (KBr) 3450 (br), 3250, 3040, 1660, 1630, 1605, 1570, 1485 cm$^{-1}$. MS (DCI/$NH_3$) 257 (M+$NH_4^+$, 20), 240 (M+H$^+$, 10), 196 (70), 102 (100). Anal. Calcd for: $C_{15}H_{13}NO_2$: C, 75.30; H, 5.48; N, 5.85. Found: C, 74.72; H, 5.62; N, 5.56.

EXAMPLE 37

Preparation of 3-(4-biphenyl)propanohydroxamic acid

Step 1: 3-(4-biphenyl)propanoic acid.

Hydrogenation of 4-phenylcinnamic acid (ethyl acetate, 10% Pd/C, 4 atm $H_2$) provided 3-(4-biphenyl)propanoic acid.

Step 2: 3-(4-biphenyl)propanohydroxamic acid.

The desired compound was prepared according to the method of Example 37, except substituting 3-(4-biphenyl) propanoic acid, prepared as in step 1, for 4-phenylcinnamic acid. $^1H$ NMR (DMSO-d6) δ 2.29 (t, 2H, J=7 Hz), 2.84 (t, 2H, J=7 Hz), 7.29 (d, 2H, J=6 Hz), 7.34 (d, 1H, J=5 Hz), 7.46 (t, 2H, J=5 Hz), 7.57 (d, 2H, J=6 Hz), 7.63 (d, 2H, J=5 Hz), 8.72 (s, 1H), 10.39 (s, 1H), MS (DCI/$NH_3$) 259 (M+$NH_4^+$, 100), 242 (M+H⁺, 5). Anal. Calcd for $C_{15}H_{15}NO_2 \cdot 0.25$ $H_2O$: C, 73.30; H, 6.36; N, 5.70. Found: C, 72.87; H, 6.05; N, 5.25.

EXAMPLE 38

Preparation of 5-(4-biphenyl)pentanohydroxamic acid

Step 1: 4-pentynoic acid benzyl ester.

To a solution in dichloromethane (25 mL) containing a few drops DMF of 4-pentynoic acid (2.49 g, 23.4 mmol) was added oxalyl chloride (2.2 mL, 25 mmol). The reaction mixture was stirred for 1.5 hours and benzyl alcohol (3.9 mL, 38 mmol) was added via syringe. The reaction mixture was stirred for 6 hours and then was extracted with saturated aqueous sodium carbonate. The organic phase was dried over $MgSO_4$, filtered, and concentrated in vacuo to give 4-pentynoic acid benzyl ester (5.94 g) as a yellow liquid.

Step 2: 5-(4-biphenyl)pentynoic acid benzyl ester.

To a mixture in triethylamine (125 mL) of 4-pentynoic acid benzyl ester (4.70 g, 25 mmol), 4-bromobiphenyl (5.80 g, 24.9 mmol), and bis(triphenylphosphine)palladium(II) chloride (0.97 g, 1.4 mmol) was added phenothiazine (10 mg) and the mixture was warmed to reflux. The reaction mixture was heated at reflux for 4 hours, and then was cooled to ambient temperature, filtered, and concentrated in vacuo. Chromatography on silica gel (30% dichloromethane/hexanes) gave 5-(4-biphenyl)pentynoic acid benzyl ester (0.70 g) as a white solid.

step 3: 5-(4-biphenyl)pentanoic acid.

Hydrogenation of 5-(4-biphenyl)pentynoic acid benzyl ester (ethyl acetate, 10% Pd/C, 4 atm $H_2$) provided 5-(4-biphenyl)pentanoic acid.

Step 4: 5-(4-biphenyl)pentanohydroxamic acid.

The desired compound was prepared according to the method of Example 37, except substituting 5-(4-biphenyl)pentanohydroxamic acid, prepared as in step 3, for 4-phenylcinnamic acid. mp 158°–159° C. ¹H NMR (DMSO-d6) δ 1.54 (m, 4H), 1.97 (t, 2H, J=7 Hz), 2.59 (t, 2H, J=7 Hz), 7.27 (d, 2H, J=7 Hz), 7.37 (m, 1H), 7.44 (t, 2H, J=7 Hz), 7.57 (d, 2H, J=7 Hz), 7.64 (d, 2H, J=7 Hz), 8.68 (s, 1H), 10.36 (s, 1H). IR (KBr) 3280, 3050, 3030, 2920, 2850, 1660, 1620, 1485 cm⁻¹. MS (DCI/NH₃) 287 (M+NH₄⁺, 100), 270 (M+H⁺, 15). Anal. Calcd for $C_{17}H_{19}NO_2 \cdot 0.5$ $H_2O$: C, 73.36; H, 7.24; N, 5.03. Found: C, 73.70; H, 7.11; N, 5.20.

EXAMPLE 39

Preparation of 5-[4-(4-fluorophenyl)phenoxy] pentanohydroxamic acid

Step 1: 5-(4-iodophenoxy)pentanoic acid.

The desired compound was prepared according to the method of Example 2, steps 1 and 2, except substituting 4-iodophenol for 3-phenylphenol, and substituting methyl 5-bromovalerate for ethyl 4-bromobutyrate.

Step 2: O-tert-butyl 5-(4-iodophenoxy)pentanohydroxamic acid.

A mixture of 5-(4-iodophenoxy)pentanoic acid (6.00 g, 18.8 mmol) and excess thionyl chloride was heated at reflux for 30 minutes. The reaction mixture was cooled to ambient temperature and concentrated in vacuo. The residue was azeotroped three times with ethyl ether and then was taken up in THF. To the acid chloride solution was added an aqueous solution of O-tert-butylhydroxylamine (24 mmol; prepared by adding aqueous 3M NaOH to an aqueous solution of O-tert-butylhydroxylamine hydrochloride) and the cloudy solution was stirred for 20 hours. The reaction mixture was poured into a mixture of ethyl acetate and saturated aqueous $NH_4Cl$. The organic phase was washed with water and brine, dried over $MgSO_4$, filtered, and concentrated in vacuo to give O-tert-butyl 5-(4-iodophenoxy)pentanohydroxamic acid (6.52 g).

Step 3: O-tert-butyl 5-[4-(4-fluorophenyl)phenoxy] pentanohydroxamic acid.

The desired compound was prepared according to the method of Example 9, step 1, except substituting O-tert-butyl 5-(4-iodophenoxy)pentanohydroxamic acid, prepared as in step 2, for 4-(4-iodophenoxy)butanoic acid ethyl ester and substituting toluene for DME.

Step 4: 5-[4-(4-fluorophenyl)phenoxy]pentanohydroxamic acid.

A solution in trifluoroacetic acid of O-tert-butyl 5-[4-(4-fluorophenyl)phenoxy]pentanohydroxamic acid (0.41 g, 1.1 mmol) was stirred overnight. The reaction mixture was concentrated in vacuo and the residue was suspended in acetonitrile and stirred for 30 minutes. The solid was filtered and dried in vacuo to give 5-[4-(4-fluorophenyl)phenoxy] pentanohydroxamic acid (128 mg) as a white solid. mp 160°–162° C. ¹H NMR (DMSO-d6) δ 10.378 (s, 1H), 8.69 (s, 1H), 7.66–7.63 (m, 2H), 7.57–7.55 (d, 2H, J=8.8 Hz), 7.27–7.21 (t, 2H, J=8.8 Hz), 7.02–6.99 (d, 2H, J=8.8 Hz), 4.02–3.98 (t, 2H, J=5.9 Hz), 2.04–2.00 (t, 2H, J=7 Hz), 1.68–1.66 (m, 4H). ¹³C NMR (DMSO-d6) δ 21.76, 28.15, 31.87, 7.11, 114.85, 115.38, 115.66, 118.34, 127.66, 127.94, 128.03, 131.04, 136.20, 136.33, 158.18, 159.76, 162.98, 168.87. MS (DCI/NH₃) 304 (M+H)⁺, 321 (M+NH₄)⁺. Anal. Calcd for $C_{17}H_{18}NO_3F$: C, 67.31; H, 5.98; N, 4.61. Found: C, 7.19; H, 6.03; N, 4.40.

EXAMPLE 40

Preparation of 4-(2-hydroxy-4-phenylphenoxy) butanohydroxamic acid

Step 1: 4-(2-hydroxy-4-phenylphenoxy)butanoic acid.

The desired compound was prepared as a 1:1 mixture with 4.(2-hydroxy-5-phenylphenoxy)butanoic acid, as described in Example 1, steps 1 and 2, except substituting 1,2-dihydroxy-4-biphenyl for 4-phenylphenol.

Step 2: 4-(2-hydroxy-4-phenylphenoxy)butanohydroxamic acid.

A suspension of the 4-(2-hydroxy-4-phenylphenoxy) butanoic acid and 4-(2-hydroxy-5-phenylphenoxy)butanoic acid mixture prepared in step 1 (0.507 g, 1.86 mmol) in trifluoroacetic anhydride (10 mL) was stirred for 15 minutes at 0° C. and 90 minutes at ambient temperature. The reaction mixture was concentrated in vacuo and the residue was dissolved in THF (10 mL). In a separate flask, 4-methylmorpholine (1.2 mL, 11 mmol) was added to a solution of hydroxylamine hydrochloride (0.70 g, 10 mmol) in water (4 mL). The aqueous hydroxylamine solution was decanted into the mixed anhydride solution and followed with a THF rinse (15 mL). The reaction mixture was stirred for 3 hours and then was partitioned between saturated aqueous $NH_4Cl$ and ethyl acetate. The organic phase was dried over $Na_2SO_4$, filtered, and concentrated in vacuo to give an off-white foam (0.52 g). The 1:1 mixture of 4-(2-hydroxy-4-phenylphenoxy)butanohydroxamic acid and 4-(2-hydroxy-5-phenylphenoxy)butanohydroxamic acid was purified by high performance liquid chromatography. The fractions enriched in 4-(2-hydroxy-4-phenylphenoxy) butanohydroxamic acid were combined to give 82 mg of a 2:1 mixture. mp 118°–122° C. ¹H NMR(DMSO-d6) δ 1.96 (p, 2H, J=7 Hz), 2.15 (t, 2H, J=7 Hz), 4.04 (t, 2H, J=7 Hz), 6.86 (d, 1H, J=7 Hz), 7.07 (dd, 1H, J=3, 7 Hz), 7.16 (d, 1H, J=3 Hz), 7.28 (m, 1H), 7.39 (t, 2H, J=7 Hz), 7.59 (d, 2H, J=7 Hz), 9.0 (bds, 2H), 10.42 (s, 1H). $^{13}$C NMR (DMSO-d6) δ 24.98, 28.83, 67.92, 112.36, 116.00, 119.38, 126.11, 126.41, 128.70, 131.49, 140.31, 146.68, 147.00, 168.87. MS (DCI/NH$_3$) 305 (M+NH$_4^+$, 45), 289 (M+NH$_4$–O$^+$, 20), 288 (M+H$^+$, 15), 287 (M+NH$_4$–H$_2$O$^+$, 10), 244 (100). Anal. Calcd for C$_{16}$H$_{17}$NO$_4$•H$_2$O: C, 62.94; H, 6.27; N, 4.59. Found: C, 63.17; H, 5.74; N, 4.55.

EXAMPLE 41

Preparation of 4-(2-hydroxy-5-phenylphenoxy) butanohydroxamic acid

The fractions enriched in 4-(2-hydroxy-5-phenylphenoxy)butanohydroxamic acid from the chromatography in Example 46 were combined to give 10 mg of a 3:1 mixture. mp 148°–152° C. $^1$H NMR (DMSO-d6) δ 1.94 (p, 2H, J=7 Hz), 2.18 (t, 2H, J=7 Hz), 3.98 (t, 2H, J=7 Hz), 6.97 (d, 1H, J=7 Hz), 7.02 (d, 1H, J=3 Hz), 7.08 (d, 1H, J=3 Hz), 7.29 (d, 1H, J=7 Hz), 7.41 (t, 2H, J=7 Hz), 7.53 (d, 2H, J=7 Hz), 8.71 (s, 1H), 8.99 (s, 1H), 10.41 (s, 1H). $^{13}$C NMR (DMSO-d6) δ 24.93, 28.76, 67.85, 113.90, 114.11, 118.34, 126.09, 126.63, 128.74, 133.27, 140.07, 146.44, 147.08, 168.84. MS (DCI/NH$_3$) 305 (M+NH$_4^+$, 100), 288 (M+H$^+$, 25). Anal. Calcd for C$_{16}$H$_{17}$NO$_4$•⅔ H$_2$O: C, 64.21; H, 6.17; N, 4.68. Found: C, 64.34; H, 5.97; N, 4.72.

EXAMPLE 42

Preparation of 3-[4-(3-cyanomethylphenyl) phenoxyl]propanohydroxamic acid

Step 1: 3-(4-iodophenoxy)propanoic acid.

The desired compound was prepared according to the method of Example 23, step 1, except substituting 4-iodophenol for 4-phenylphenol.

Step 2: O-tert-butyl 3-(4-iodophenoxy)propanohydroxamic acid.

A suspension of 3-(4-iodophenoxy)propanoic acid (1.00 g, 3.42 mmol) in thionyl chloride (6.0 mL) was heated at reflux for 30 minutes. The reaction mixture was cooled to ambient temperature, diluted with ethyl ether, and concentrated in vacuo. The residue was azeotroped three times with ethyl ether, dried under high vacuum, and taken up in dichloromethane (7 mL) under N$_2$. To the solution was added a solution in dichloromethane of O-tert-butylhydroxylamine (8.60 mmol; prepared by dissolving O-tert-butylhydroxylamine hydrochloride in water, making the free base with aqueous 10% Na$_2$CO$_3$, and extracting the solution with dichloromethane, and drying the organic solution over MgSO$_4$), and the reaction mixture was stirred for two hours. The reaction mixture was washed with saturated aqueous NaHCO$_3$ and brine, dried over Na$_2$SO$_4$, filtered, and concentrated in vacuo to give a yellow oil which crystallized on standing to give O-tert-butyl 3-(4-iodophenoxy)propanohydroxamic acid (1.22 g, 98%).

Step 3: O-tert-butyl 3-[4-(3-cyanomethylphenyl)phenoxyl] propanohydroxamic acid.

The desired compound was prepared according to the method of Example 4, steps 2 and 3, except substituting O-tert-butyl 3-(4-iodophenoxy)propanohydroxamic acid, prepared as in step 2, for 4-(4-iodophenoxy)butanoic acid ethyl ester, and substituting 3-iodophenylacetonitrile for 3-iodobenzonitrile.

Step 4: 3-[4-(3-cyanomethylphenyl)phenoxy] propanohydroxamic acid.

A solution of O-tert-butyl 3-[4-(3-cyanomethylphenyl) phenoxy]propanohydroxamic acid (0.043 g, 0.12 mmol) in 1:1 trifluoroacetic acid-dichloromethane was stirred overnight at ambient temperature. The reaction mixture was filtered, concentrated in vacuo, and azeotroped with dichloromethane and dichloromethane-ethyl ether. Chromatography on silica gel (40:1, then 20:1 dichloromethane-methanol, both containing 0.25% acetic acid) gave 3-[4-(3-cyanomethylphenyl)phenoxy]propanohydroxamic acid (16 mg, 44%). $^1$H NMR (DMSO-d6) δ 2.45 (t, 2H, J=6.0 Hz), 4.08 (s, 2H), 4.23 (t, 2H, J=6.0 Hz), 7.02 (d, 2H, J=8.8 Hz), 7.29 (d, 1H, J=7.5 Hz), 7.46 (t, 1H, J=8.0 Hz), 7.57 (d, 1H, J=6 Hz), 7.58 (s, 1H), 7.60 (d, 2H, J=8.8 Hz); 8.84 (br s, 1H), 10.53 (br s, 1H). IR (microscope) 3245 (br), 2924 (m), 2251 (w), 1643 (s), 1608 (s), 1518 (s), i483 (m), 1244 (s), 784 (m) cm$^{-1}$. MS (DCI/NH$_3$) 314 (M+NH$_4$)$^+$. Anal. Calcd for C$_{17}$H$_{16}$N$_2$O$_3$•0.70 H$_2$O•0.20 tBuOH: C, 66.04; H, 6.04; N, 8.65. Found: C, 65.93; H, 5.64; N, 8.30.

EXAMPLE 43

Preparation of 2-tert-butyloxycarbonylmethyl-4-[4-(4-cyanophenyl)phenoxy]butanohydroxamic acid Step 1: N-:[4-(4-(4-cyanophenyl)phenoxy)butanoyl]-(S)-(–)-4-benzyl-2-oxazolidinone.

To a –70° C. solution in THF (100 mL) of 4-[4-(4-cyanophenyl)phenoxy]butanoic acid (1.00 g, 3.66 mmol), prepared as in Example 3, was added triethylamine (0.64 mL, 4.62 mmol) and pivaloyl chloride (0.49 mL, 3.91 mmol). The reaction mixture was stirred for 15 minutes at –70° C., 45 minutes at 0° C., and then was cooled back to –70° C. In a separate flask, n-butyllithium (2.5M in hexanes, 2.56 mL, 6.40 mmol) was added via syringe to a –78° C. a solution in THF (50 mL) of (S)-(–)-4-benzyl-2-oxazolidinone. The oxazolidinone anion solution was then added to the mixed anhydride solution via cannula. The reaction mixture was then warmed slowly to ambient temperature and stirred overnight. The reaction mixture was quenched with aqueous 1M HCl and extracted with ethyl ether. The organic phase was washed with brine, dried over MgSO$_4$, filtered, and concentrated in vacuo. The resulting white solid was azeotroped with ethyl ether and purified by chromatography on silica gel (2% methanol-dichloromethane) to give N-[4-(4-(4-cyanophenyl)phenoxy) butanoyl]-(S)-(–)-4-benzyl-2-oxazolidinone (1.30 g, 82%).

Step 2: N-[2-tert-butyloxycarbonylmethyl-4-(4-(4-cyanophenyl)phenoxy)butanoyl]-(S)-(–)-4-benzyl-2-oxazolidinone.

To a –78° C. solution in THF (50 mL) of N-[4-((4-cyanophenyl)phenoxy)butanoyl]-(S)-(–)-4-benzyl-2-oxazolidinone (1.30 g, 2.95 mmol), prepared as in step 1, was added sodium bis(trimethylsilyl)amide (1.0M, 3.25 mL, 3.25 mmol) and the reaction mixture was stirred for 20 minutes. Neat tert-butyl bromoacetate (0.50 mL, 3.25 mmol) was added quickly dropwise and the reaction mixture was stirred for 20 minutes at –78° C. and then was warmed to –50° C. over 3 hours. The reaction mixture was quenched with acetic acid (5 mL) in ethyl ether (40 mL), warmed to ambient temperature, and extracted with brine. The organic phase was concentrated in vacuo to give a viscous oil. The oil was crystallized from ethyl acetate-ethyl ether to give a solid (10 g). Chromatography on silica gel (1:3 ethyl acetate-hexanes) gave N-[2-tert-butyloxycarbonylmethyl-4-(4-(4-cyanophenyl)phenoxy)butanoyl]-(S)-(–)-4-benzyl-2-oxazolidinone (7.18 g).

Step 3: 2-tert-butyloxycarbonylmethyl-4-[4-(4-cyanophenyl)phenoxy]butanoic acid.

To a 0° C. solution in THF (200 mL) of N-[2-tert-butyloxycarbonylmethyl-4-(4-(4-cyanophenyl)phenoxy)butanoyl]-(S)-(−)-4-benzyl-2-oxazolidinone (7.05 g, 12.7 mmol) was added 30% aqueous $H_2O_2$ (3.0 mL, 50.8 mmol) and 1M aqueous LiOH (20.3 mL, 20.3 mmol) and the reaction mixture was stirred for one hour. The reaction mixture was quenched with saturated aqueous $NaHSO_3$ and diluted with dichloromethane. The aqueous phase was made basic with aqueous 2N NaOH and extracted twice with dichloromethane. The organic extracts were discarded and the aqueous phase was cooled to 0° C. and acidified with aqueous 2N HCl. The aqueous phase was extracted with dichloromethane and THF/dichloromethane. The combined organic extracts were dried over $MgSO_4$, filtered, and concentrated in vacuo. Chromatography on silica gel (dichloromethane/10% THF/1% methanol) gave 2-tert-butyloxycarbonylmethyl-4-[4-(4-cyanophenyl)phenoxy]butanoic acid (2.6 g, 52%).

Step 4: 2-tert-butyloxycarbonylmethyl-4-[4-(4-cyanophenyl)phenoxyl]butanohydroxamic acid.

The desired compound was prepared according to the method of Example 29, step 5, except substituting 2-tert-butyloxycarbonylmethyl-4-[4-(4-cyanophenyl)phenoxy]butanoic acid, prepared as in step 3, for 3-methyl-2-[4-(4-cyanophenyl)phenoxy]butanoic acid. $^1$H NMR (DMSO-d6) δ 1.38 (s, 9H), 1.76–1.98 (m, 2H), 2.36 (dd, 1H, J=6, 15 Hz), 2.45–2.58 (m, 1H), 2.58–2.70 (m, 1H), 3.90–4.50 (m, 2H), 7.03 (d, 2H, J=9 Hz), 7.72 (d, 2H, J=9 Hz), 7.82–7.91 (m, 4H), 10.58 (s, 1H). MS (DCI/NH$_3$) 411 (M+H)$^+$, 428 (M+NH$_4$)$^+$, 372, 354. Anal Calcd. for $C_{23}H_{26}N_2O_5 \cdot 1.25 H_2O$: C, 63.80; H, 6.63; N, 6.46. Found: C, 63.67; H, 6.17; N, 6.41.

EXAMPLE 44

Preparation of 3-[4-(4-cyanomethylphenyl)phenoxyl]propanohydroxamic acid

The desired compound was prepared according to the method of Example 43, except substituting 4-iodophenylacetonitrile for 3-iodophenylacetonitrile. $^1$H NMR (DMSO-d6) δ 2.44 (t, 2H, J=6. 1 Hz), 4.05 (s, 2H), 4.23 (t, 2H, J=6.0 Hz), 7.00 (d, 2H, J=8.8 Hz), 7.40 (d, 2H, J=8.5 Hz), 7.60 (d, 2H, J=8.8 Hz), 7.64 (d, 2H, J=8.1 Hz), 8.83 (s, 1H), 10.52 (s, 1H). IR (microscope) 3218 (m), 3195 (m), 2252 (w), 1632 (s), 804 (m) cm$^{-1}$. MS (DCI/NH$_3$) 298 (M+NH$_4$–O)$^+$, 314 (M+NH$_4$)$^+$. Anal. Calcd for $C_{17}H_{16}N_2O_3 \cdot 0.60H_2O \cdot 0.20$: $CF_3CO_2H$ C, 63.34; H, 5.32; N, 8.49. Found: C, 63.33; H, 4.98; N, 8.52.

EXAMPLE 45

Preparation of 2-hydroxy-3-[(4-phenyl)phenoxy]propanohydroxamic acid

Step 1: 1,1-Dimethoxy-2-(4-biphenyloxy)ethane.

4-Phenylphenol (1.70 g, 10 mmol) and cesium carbonate (3.91 g (12 mmol) were stirred at room temperature under a nitrogen atmosphere in 20 mL of dimethylformamide until it appeared that no more solid was dissolving. At that point, 1.42 mL (12 mmol) of bromoacetaldehyde dimethyl acetal (2.03 g, 12 mmol) were added to the mixture via syringe and the resulting brown suspension was stirred at room temperature overnight. The mixture was then heated under reflux for two hours and then stirred at room temperature overnight. At the end of this period, 100 mL of water and 200 mL of diethyl ether were added; the organics were extracted into the ether layer, which was separated, dried over anhydrous sodium sulfate and evaporated to yield 2.10 g (81% yield) of dimethoxy-2-(4-biphenyloxy)ethane.

Step 2: 4-Biphenyloxyacetaldehyde.

The acetal from Step 1 (2.10 g) was dissolved in 10 mL of tetrahydrofuran and 1 mL of distilled water was added to the yellow solution, followed by 1 mL of concentrated hydrochloric acid. This mixture was stirred rapidly overnight, then a small amount of saturated aqueous brine solution was added to the reaction mixture, followed by 50 mL of diethyl ether. The organics were extracted into the ether layer and the aqueous layer was washed twice more with diethyl ether. The ether layers were combined, dried over anhydrous magnesium sulfate, and evaporated. The residue was triturated with a 10% solution if isopropyl alcohol in chloroform, leaving a white solid. This solid was again triturated with a small amount of methanol in dichloromethane. The yield of filtrates from the above two triturations was 1.84 g (71% ) of 4-biphenyloxyacetaldehyde.

Step 3: 2-(4-phenylphenoxy)ethane cyanohydrin.

The aldehyde from Step 2 (1.84 g) was placed in a 250 mL three-necked flask and 65 ml of toluene were added. The resulting mixture was stirred under nitrogen at room temperature until a cloudy yellow suspension resulted. Diethylaluminum cyanide solution (1M in toluene, Aldrich Chemical Co., Milwaukee, Wis.) (11.3 mL 11.3 mmol) was added to the stirred mixture in a dropwise manner over a period of six minutes. The resulting mixture was stirred at −15° C. for one hour and then at room temperature for an additional thirty minutes. The mixture was cooled in an ice bath and 25 mL of saturated aqueous Rochelle salt solution was added in a dropwise manner over eight minutes. At the end of this time, the mixture was allowed to warm to room temperature and was stirred at this temperature for thirty minutes. A mixture of aqueous Rochelle salt solution and 100 mL of ethyl acetate were added to the mixture. The organic layer was set aside and the aqueous layer extracted with ethyl acetate. The ethyl acetate solutions were combined, dried over anhydrous sodium sulfate, filtered and evaporated to yield 1.70 g of light yellow residue.

This solid was taken up in a mixture of hexane, ethyl acetate and dichloromethane and the resulting solution charged to a column of 50 g of silica. The mixture was eluted from the column (30 mL 15% ethyl acetate in hexanes; 730 mL: 50% ethyl acetate in hexanes; and 1 liter, 100% isopropyl alcohol) to yield 1.43 g (68%) 2-(4-phenylphenoxy)ethane cyanohydrin as a white solid.

Step 4: 2-hydroxy-3-[(4-phenyl)phenoxy]propanoic acid.

Anhydrous methanol (140 mL, maintained at a temperature below 25° C.) was saturated with hydrogen chloride gas in a 1-liter, three-necked flask. This solution was then added in one portion to a solution of the cyanohydrin obtained from Step 3. The resulting mixture was maintained at about 0° C. and stirred under nitrogen overnight. After this time, the mixture was allowed to warm to about 20° C. where it was stirred for several hours. Water (150 mL) was added and the resulting mixture was stirred for thirty minutes at 20° C.

After this time the mixture was heated under reflux for three hours. The mixture. was cooled to room temperature and evaporated to dryness under vacuum to yield a yellow, semi-solid residue. This material was partitioned between 1M aqueous NaOH and dichloromethane and the organic layer was set aside. The aqueous layer was acidified with aqueous HCl and extracted twice with dichloromethane and once with a 10% solution of isopropyl alcohol in chloroform. The aqueous layer was then extracted twice with ethyl acetate and these organic extracts combined with those described above. The overall yield of 2-hydroxy-3-[(4-phenyl)phenoxy]propanoic acid was 1.41 g (91%).

Step 5: 2-hydroxy3-[(4-phenyl)phenoxy]propanohydroxamic acid.

2-hydroxy-3-[(4-phenyl)phenoxy]propanoic acid (517 mg, 2 mmol) from Step 4 was mixed with 740 mg (5.48 mmol) of hydroxybenzotriazole hydrate (Aldrich Chemical Co., Milwaukee, Wis.) and the solid mixture was dissolved in 20 mL of dichloromethane. This mixture was stirred under a nitrogen atmosphere at room temperature and then 5 mL of dimethylformamide and 291.6 g, 2.9 mmol) of 4-methylmorpholine were added. This was followed by addition of 353 mg of O-tert-butyldimethylsilyl hydroxylamine (Aldrich Chemical Co., Milwaukee, Wis.) dissolved in 5 mL of dichloromethane.

To the resulting cloudy yellow suspension was added, as a solid, 553 mg (2.9 mmol) of 1-(3-dimethylaminopropyl)-3-ethylcarbodiimide ("EDCI," Aldrich Chemical Co., Milwaukee, Wis.). Upon addition of the EDCI, the mixture became first, a clear yellow, then a clear orange solution, and finally, a cloudy orange suspension. This mixture was stirred at room temperature for two hours and then diluted with 30 mL of saturated aqueous ammonium chloride solution. The organic layer was separated and set aside. The aqueous layer was washed with dichloromethane and the two organic solution combined, dried over anhydrous magnesium sulfate and concentrated to yield 970 mg of solid residue.

This solid residue was taken up in a solution of 1% methanol in dichloromethane, and methanol carefully added until only a slight cloudiness remained. This mixture was loaded on a column of 110 g of silica and eluted (25 mL of 1% methanol in dichloromethane (fractions 1–32), 25 mL of 5% methanol in dichloromethane (fractions 33–99), and 700 mL of 100% isopropyl alcohol (fraction 100). Fractions 54–69 were combined to yield 15.6 mg of 2-hydroxy-3-[(4-phenyl)phenoxy]propanohydroxamic acid as a white solid having a melting point of 138.7° C.–140.5° C. $^1$H NMR (DMSO-d6): δ 0.87 (s, 1H), 4.03–4.28 (c, 2H), 5.79 (d, 1H, J=6 Hz), 7.00 (s, 1H), 7.03 (s, 1H), 7.30 (t, 1H, J=7.5 Hz), 7.43 (t, 1H), J=7.5,Hz), 7.57–7.65 (c, 4H), 8.35 (s, 1H), 10.66 (s, 1H); Infrared spectrum (KBr pellet) 3420, 3260, 1600, 1520, 1480, 1450, 1290, 1270, 1250, 1110, 1050, 830, 780, 700 cm$^{-1}$; Mass spectrum: (DCI/NH$_3$): 291 (M+NH$_4$+), 274.1079.

The foregoing examples are merely illustrative of the invention and are not intended to limit the invention to the disclosed compounds. Variations and changes which are obvious to one skilled in the art are intended to be within the scope and nature of the invention which is defined in the appended claims.

We claim:
1. A compound of formula

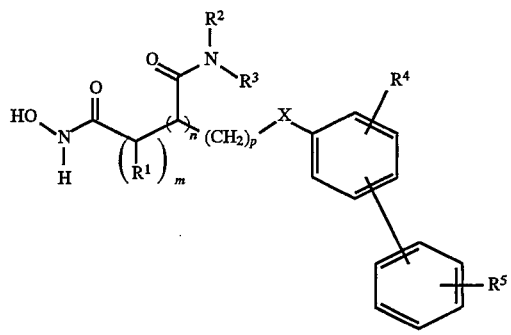

or a pharmaceutically acceptable salt thereof
where m and n are independently 0 or 1;
p is 0–6, with the proviso that m, n, and p cannot simultaneously be zero;
$R^1$ is selected from the group consisting of
(a) hydrogen;
(b) alkyl of one to six carbon atoms;
(c) (alkylene) of two to six carbon atoms;
(d) hydroxy;
(e)

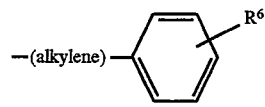

where the alkylene portion is of one to six carbon atoms, and $R^6$ is selected from the group consisting of alkyl of one to six carbon atoms, haloalkyl of one to six carbon atoms, alkoxy of one to six carbon atoms, and hydroxy;
(f)

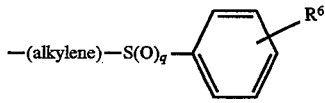

wherein q is 0, 1 or 2, the alkylene portion is of one to six carbon atoms, and $R^6$ is defined above;
(g) -(alkylene)-CO$_2$R$^7$ wherein the alkylene portion is of one to six carbon atoms, and $R^7$ is hydrogen or alkyl of one to six carbon atoms;
$R^2$ and $R^3$ are independently selected from the group consisting of
(a) hydrogen;
(b) alkyl of one to six carbon atoms;
(c) phenyl;
(d) phenyl substituted with
halogen,
alkyl of one to six carbon atoms,
haloalkyl of one to six carbon atoms,
alkoxy of one to six carbon atoms, or
hydroxy;
(e) pyridyl, and
(f) pyridyl substituted with
halogen, alkyl of one to six carbon atoms,
haloalkyl of one to six carbon atoms, or
alkoxy of one to six carbon atoms; or $R^2$ and $R^3$ taken together with the nitrogen atom to which they are attached define a 5- or 6-membered saturated heterocyclic ring in which the heterocyclic ring optionally contains an additional heteroatom selected from the group consisting of —$NR^8$ wherein $R^8$ is hydrogen or alkyl of one to six carbon atoms, —O—, —S—, or —S(O)$_r$— wherein r is 1 or 2;

X is absent or is selected from the group consisting of (a) —O—;

(b) —NH—; and (c) —S—;

with the provisos that (a) when X is oxygen, and m and n are zero, p is an integer of two to six, inclusive, and (b) when X is oxygen and m is one and n is zero; then p is an integer of one to six, inclusive;

$R^4$ and $R^5$ are independently selected from the group consisting of (a) hydrogen;

(b) alkyl of one to six carbon atoms;

(c) halogen;

(d) cyano;

(e) cyanoalkyl of one to six carbon atoms;

(f) haloalkyl of one to six carbon atoms, (g) hydroxy, and (h) alkoxy of one to six carbon atoms.

2. A compound or pharmaceutically acceptable salt thereof as defined by claim 1 of formula

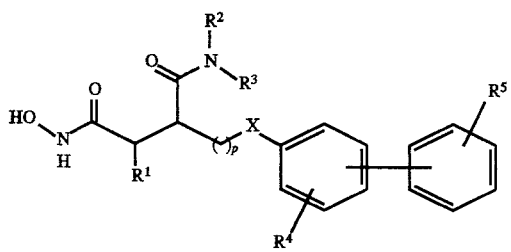

or a pharmaceutically acceptable salt thereof wherein p is an integer of 0–6, inclusive.

3. A compound as defined by claim 1 or pharmaceutically acceptable salt thereof wherein $R^1$ is selected from the group consisting of (a) hydrogen, (b) alkyl of one to six carbon atoms, and (c) alkenyl of two to six carbon atoms.

4. A compound or pharmaceutically acceptable salt thereof as defined by claim 3 wherein $R^2$ and $R^3$ are independently selected from hydrogen and alkyl of one to six carbon atoms.

5. A compound or pharmaceutically acceptable salt thereof as defined by claim 4 wherein X is —O—.

6. A compound or pharmaceutically acceptable salt thereof as defined by claim 1 having the formula

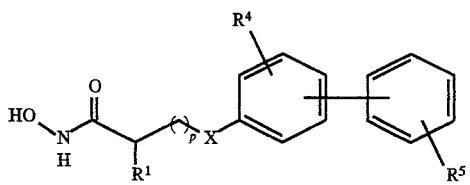

wherein p is 1–6.

7. A compound or pharmaceutically acceptable salt thereof as defined by claim 6 wherein $R^1$ is selected from the group consisting of (a) hydrogen, (b) alkyl of one to six carbon atoms, and (c) alkenyl of two to six carbon atoms.

8. A compound or pharmaceutically acceptable salt thereof as defined by claim 6 wherein X is absent.

9. A compound or pharmaceutically acceptable salt thereof as defined by claim 6 wherein X is —O—.

10. A method for inhibiting matrix metalloproteinases in a mammal in need of such treatment, comprising administering to the mammal a therapeutically effective amount of a compound of claim 1.

11. An composition for inhibiting matrix metalloproteinases comprising a pharmaceutical carrier and a therapeutically effective amount of a compound of claim 1.

12. A method for inhibiting TNFα secretion in a mammal in need of such treatment, comprising administering to the mammal a therapeutically effective amount of a compound of claim 1.

13. A composition for inhibiting TNFα secretion comprising a pharmaceutical carrier and a therapeutically effective amount of a compound of claim 1.

14. A compound or pharmaceutically acceptable salt thereof selected from the group consisting of 4-(4-phenylphenoxy)butanohydroxamic acid,
4-(3-phenylphenoxy)butanohydroxamic acid,
4-[4-(4-cyanophenyl)phenoxy]butanohydroxamic acid,
4-[4-(3-cyanophenyl)phenoxy]butanohydroxamic acid,
4-[4-(4-cyanomethylphenyl)phenoxy]butanohydroxamic acid,
4-[4-(3-cyanomethylphenyl)phenoxy]butanohydroxamic acid,
4-[4-(4-chlorophenyl)phenoxy]butanohydroxamic acid,
4-[4-(4-propylphenyl)phenoxy]butanohydroxamic acid,
4-[4-(4-methoxyphenyl)phenoxy]butanohydroxamic acid,
7-(4-phenylphenoxy)heptanohydroxamic acid,
7-[4-(4-cyanophenyl)phenoxy]heptanohydroxamic acid,
5-[3-(4-fluorophenyl)phenoxy]pentanohydroxamic acid,
5-[3-(3-cyanophenyl)phenoxyl]pentanohydroxamic acid,
5-[3-(4-cyanophenyl)phenoxy]pentanohydroxamic acid,
4-[3-(4-fluorophenyl)phenoxy]butanohydroxamic acid,
4-[3-(4-cyanophenyl)phenoxy]butanohydroxamic acid,
4-[3-(3-cyanophenyl)phenoxy]butanohydroxamic acid,
5-[3-phenylphenoxy]pentanohydroxamic acid,
5-[4-phenylphenoxy]pentanohydroxamic acid,
5-[4-(4-cyanophenyl)phenoxy]pentanohydroxamic acid,
6-[4-phenylphenoxy]hexanohydroxamic acid,
6-[4-(4-cyanophenyl)phenoxyl]hexanohydroxamic acid,
3-(4-phenylphenoxy)propanohydroxamic acid,
3-(3-phenylphenoxy)propanohydroxamic acid,
3-[4-(4-cyanophenyl)phenoxy]propanohydroxamic acid,
3-[4-(4-methoxyphenyl)phenoxy]propanohydroxamic acid,
3-[4-(4-fluorophenyl)phenoxy]propanohydroxamic acid,
(S)2-methyl-3-(4-phenylphenoxy)propanohydroxamic acid,
3-(N-methylcarboxamido)-5-[4-(4-cyanophenyl)phenoxy]pentanohydroxamic acid, 3-(4-biphenylthio)propanohydroxamic acid,
2-(4-biphenylthio)ethanohydroxamic acid,
3-(4-biphenylamino)propanohydroxamic acid,
2-(4-biphenyl)ethanohydroxamic acid,
4-(4-biphenyl)butanohydroxamic acid,
4-[4-(4-cyanophenyl)phenyl]butanohydroxamic acid,
3-(4-biphenyl)propanohydroxamic acid,
5-(4-biphenyl)pentanohydroxamic acid,
5-[4-(4-fluorophenyl)phenoxy]pentanohydroxamic acid,
4-(2-hydroxy-4-phenylphenoxy)butanohydroxamic acid,
4-(2-hydroxy-5-phenylphenoxy)butanohydroxamic acid,
3-[4-(3-cyanomethylphenyl)phenoxy]propanohydroxamic acid,
2-tert-butyloxycarbonylmethyl-4-[4-(4-cyanophenyl)phenoxy]butanohydroxamic acid,
3-[4-(4-cyanomethylphenyl)phenoxy]propanohydroxamic acid, and
2-hydroxy-3-[(4-phenyl)phenoxy]propanohydroxamic acid.

* * * * *

UNITED STATES PATENT AND TRADEMARK OFFICE
CERTIFICATE OF CORRECTION

PATENT NO. : 5,665,777
DATED : September 9, 1997
INVENTOR(S) : Fesik et al.

It is certified that error appears in the above-identified patent and that said Letters Patent is hereby corrected as shown below:

Column 42, line 50, change "phenoxyl" to --phenoxy--.

Column 42, line 59, change "phenoxyl" to --phenoxy--.

Signed and Sealed this

Seventeenth Day of February, 1998

*Attest:*

BRUCE LEHMAN

*Attesting Officer*     *Commissioner of Patents and Trademarks*